US011591382B2

(12) United States Patent
Haley et al.

(10) Patent No.: US 11,591,382 B2
(45) Date of Patent: Feb. 28, 2023

(54) EXPRESSION OF FC-CONTAINING PROTEINS

(71) Applicant: Genentech, Inc., South San Francisco, CA (US)

(72) Inventors: Benjamin Haley, San Francisco, CA (US); Zhilan Hu, Foster City, CA (US); John C. Joly, San Mateo, CA (US); Amy Y. Shen, San Mateo, CA (US); Bradley Richard Snedecor, Portola Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/761,887

(22) PCT Filed: Sep. 21, 2016

(86) PCT No.: PCT/US2016/052962

§ 371 (c)(1),
(2) Date: Mar. 21, 2018

(87) PCT Pub. No.: WO2017/053482

PCT Pub. Date: Mar. 30, 2017

(65) Prior Publication Data

US 2018/0282398 A1 Oct. 4, 2018

Related U.S. Application Data

(60) Provisional application No. 62/222,187, filed on Sep. 22, 2015.

(51) Int. Cl.

| | |
|---|---|
| ***C12N 5/00*** | (2006.01) |
| ***C07K 16/00*** | (2006.01) |
| ***C12N 15/113*** | (2010.01) |
| ***C12N 15/85*** | (2006.01) |
| ***C12P 21/02*** | (2006.01) |

(52) U.S. Cl.

CPC .......... *C07K 16/00* (2013.01); *C12N 15/1137* (2013.01); *C12N 15/85* (2013.01); *C12P 21/02* (2013.01); *C07K 2317/14* (2013.01); *C07K 2317/52* (2013.01); *C07K 2319/30* (2013.01); *C12N 2310/14* (2013.01); *C12N 2310/20* (2017.05); *C12N 2510/00* (2013.01); *C12N 2510/02* (2013.01); *C12N 2511/00* (2013.01)

(58) Field of Classification Search

CPC ............... C07K 16/00; C07K 2317/14; C07K 2317/52; C07K 2319/30; C12N 15/1137; C12N 15/85; C12N 2310/20; C12N 2310/14; C12N 2510/00; C12N 2510/02; C12N 2511/00; C12P 21/02

See application file for complete search history.

(56) References Cited

U.S. PATENT DOCUMENTS

| | | | |
|---|---|---|---|
| RE30,985 E | 6/1982 | Cartaya | |
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 4,965,195 A | 10/1990 | Namen et al. | |
| 4,968,607 A | 11/1990 | Dower et al. | |
| 5,122,469 A | 6/1992 | Mather et al. | |
| 6,037,525 A | 3/2000 | Thompson et al. | |
| 6,177,612 B1 | 1/2001 | Jordan et al. | |
| 6,239,328 B1 | 5/2001 | Thompson | |
| 6,245,974 B1 | 6/2001 | Michalowski et al. | |
| 6,388,066 B1 | 5/2002 | Bruce et al. | |
| 7,129,062 B2 | 10/2006 | Mermod et al. | |
| 7,259,010 B2 | 8/2007 | Kim et al. | |
| 7,326,567 B2 | 2/2008 | Saha | |
| 7,422,874 B2 | 9/2008 | Kim et al. | |
| 7,923,221 B1 | 4/2011 | Cabilly et al. | |
| 10,323,081 B2 | 6/2019 | Parren et al. | |
| 2013/0280274 A1 | 10/2013 | Subramanian et al. | |
| 2013/0323785 A1* | 12/2013 | Sohn .................... | C07K 14/485 435/69.4 |
| 2014/0271623 A1* | 9/2014 | Parren ................ | G01N 33/5014 424/133.1 |
| 2015/0110775 A1 | 4/2015 | Subramanian | |
| 2015/0159174 A1* | 6/2015 | Frendewey .............. | C12N 9/22 800/21 |
| 2015/0232881 A1* | 8/2015 | Glucksmann .......... | C12N 15/63 514/44 R |

FOREIGN PATENT DOCUMENTS

| | | |
|---|---|---|
| EP | 0 367 566 A1 | 5/1990 |
| EP | 0 460 846 A1 | 12/1991 |
| JP | 2014526884 A | 10/2014 |

(Continued)

OTHER PUBLICATIONS

Jin et al in "SiRNA-targeted carboxypeptidase D inhibits hepatocellular carcinoma growth", (Cell Biol Int, Apr. 30, 2013 vol. 37, No. 9, pp. 929-939; IDS reference). (Year: 2013).*

Lee et al ("CRISPSR/Cas9-mediated genome engineering of CHO cell factories: Application and perspectives" Biotechnol. J. 2015 vol. 10, pp. 979-994, Epub Jun. 9, 2015). (Year: 2015).*

Dick et al (Biotechnol Bioeng, 100, 2008, pp. 1132-1134). (Year: 2008).*

Adams, J.M. et al. (Dec. 12, 1985). "The c-myc Oncogene Driven By Immunoglobulin Enhancers Induces Lymphoid Malignancy In Transgenic Mice," *Nature* 318(6046):533-538.

(Continued)

*Primary Examiner* — Catherine S Hibbert

(74) *Attorney, Agent, or Firm* — Morrison & Foerster LLP

(57) ABSTRACT

The present invention provides compositions comprising a Fc-containing protein wherein substantially all the Fc domains have a C-terminal lysine. Further provided are host cell for producing said compositions, methods of making said host cells and compositions, and method of use thereof.

8 Claims, 7 Drawing Sheets

Specification includes a Sequence Listing.

(56) References Cited

FOREIGN PATENT DOCUMENTS

| | | | | |
|---|---|---|---|---|
| WO | WO-1987/00195 A1 | | 1/1987 | |
| WO | WO-1990/03430 A1 | | 4/1990 | |
| WO | WO-2011/064282 A1 | | 6/2011 | |
| WO | 2013004841 A1 | | 1/2013 | |
| WO | WO 2013/009648 A2 | | 1/2013 | |
| WO | WO 2013/009648 A3 | | 1/2013 | |
| WO | WO 2014/159579 A1 | | 10/2014 | |
| WO | WO-2014159579 A1 | * | 10/2014 | C07K 16/241 |

OTHER PUBLICATIONS

Aldrich, T.L. et al. (2003, e-pub. Jul. 19, 2003). "EASE Vectors for Rapid Stable Expression of Recombinant Antibodies," *Biotechnol. Prog.* 19(5):1433-1438.

Alexander, W.S. et al. (Apr. 1987). "Expression Of The c-myc Oncogene Under Control Of An Immunoglobulin Enhancer in Eμ-myc Transgenic Mice," *Mol. Cell. Biol.* 7(4):1436-1444.

Barnes, D. et al. (1980). "Methods For Growth Of Cultured Cells in Serum-Free Medium," *Anal. Biochem.*102:255-270.

Beck, A. et al. (2010). "Strategies and challenges for the next generation of therapeutic antibodies," *Nat. Rev. Immunol*, 10:345-353.

Benoist, C. et al. (Mar. 26, 1981). "In vivo Sequence Requirements Of The SV40 Early Promotor Region," *Nature* 290(5804):304-310.

Brinster, R.L. et al. (Mar. 4, 1982). "Regulation Of Metallothionein-Thymidine Kinase Fusion Plasmids Injected Into Mouse Eggs," *Nature* 296:39-42.

Carson, K.L. (2005). "Flexibility—The Guiding Principle For Antibody Manufacturing," *Nat. Biotechnol.* 23:1054-1058.

Chirino, A.J. et al. (Nov. 2004). "Characterizing Biological Products and assessing Comparability Following Manufacturing Changes," *Nat. Biotechnol.* 22(11):1383-1391.

Cosman, D. et al. (1984, e-pub. Dec. 20-27, 1984). "Cloning, Sequence and Expression Of Human Interleukin-2 Receptor," *Nature* 312:768-771.

Czajkowsky, D.M. et al. (2012). "Fc-Fusion Proteins: New Developments and Future Perspectives," *Mol. Med.* 4:1015-1028.

Deboer, H.A. et al. (Jan. 1983). "The tac Promotor: A Functional Hybrid Derived From the trp and lac Promotors," *Proc. Natl. Acad. Sci. U.S.A.* 80:21-25.

Dick Jr., L.W. et al. (Aug. 2008). "C-Terminal Lysine Variants In Fully Human Monoclonal Antibodies: Investigation Of Test Methods And Possible Causes," *Biotechnol. Bioeng.* ;100(6):1132-1143.

Doench, J.G et al. (Dec. 2014), "Rational Design Of Highly Active sgRNAs For CRISPR-Cas9-Mediated Gene Inactivation," *Nat. Biotechnol.* 32(12):1262-1267, 17 pages.

Gaj, T. et al. (Jul. 2013). "ZFN, TALEN, and CRISPR/Cas-Based Methods For Genome Engineering," *Trends Biotechnol.* 31(7):397-405.

Gluzman, Y. (Jan. 1981). "SV40-Transformed Simian Cells Support The Replication Of Early SV40 Mutants," *Cell* 23:175-182.

Grosschedl, R. et al. (Oct. 1984). "Introduction Of A μ Immunoglobulin Gene Into The Mouse Germ Line: Specific Expression In Lymphoid Cells And Synthesis Of Functional Antibody," *Cell* 38(3):647-658.

Guss, B. et al. (1986). "Structure Of The IgG-Binding Regions Of Streptococcal Protein G," *EMBO J.* 5(7):1567-1575.

Ham, R.G. et al. (1979). "[5] Media and Growth Requirements," *Meth. Enz.* 58:44-93.

Hammer, R.E. et al. (Jan. 2, 1987). "Diversity of Aipha-Fetoprotein Gene Expression in Mice Is Generated By A Combination Of Separate Enhancer Elements," *Science* 253:53-58.

Hanahan, D. (May 9, 1985). "Heritable Formation Of Pancreatic β-Cell Tumours In Transgenic Mice Expressing Recombinant Insulin/Simian Virus 40 Oncogenes," *Nature* 315(6015):115-122.

Harris, Rj. (Jun. 1995). "Processing Of C-Terminal Lysine and Arginine Residues Of Proteins Isolated From Mammalian Cell Culture," *J. Chromatogr A.* 705(1):129-134.

He, Z. et al. (2015, e-pub. Dec. 23, 2014). "Highly Efficient Targeted Charomosome Deletions Using CRISPR/Cas9," *Biotechnol. Bioeng.* 112:1060-1064.

Hu, Z. et al. (2013). "Carboxypeptidase D Is The Only Enzyme Responsible For Antibody C-Terminal Lysine Cleavage In Chinese Hamster Ovary (CHO) Cells," *Biotechnol. Prog.* 29, 27 pages.

Hu, Z. et al. (Oct. 1, 2016, e-pub. Apr. 6, 2016). "Carboxypeptidase D Is The Only Enzyme Responsible For Antibody C-Terminal Lysine Cleavage In Chinese Hamster Ovary (CHO) Cells," *Biotechnology And Bioengineering* 113(10):2100-2106.

Huse, K. et al. (2002). "Purification Of Antibodies By Affinity Chromatography," *J Biochem Bioph Meth.* 51:217-231.

Jinek, M. et al. (Jan. 29, 2013). "RNA-Programmed Genome Editing In Human Cells," *eLIFE* 2:e00471, 9 pages.

Jones, A.J.S. (1993). "Analysis Of Polypeptides and Proteins," *Adv Drug Delivery Rev.* 10:29-90.

Kelsey, G.D. et al. (1987). "Species-and Tissue-Specific Expression Of Human $\alpha_1$-Antitrypsin In Transgenic Mice," *Genes and Devel.* 1:161-171.

Kim et al. (2010, e-pub. Jun. 13, 2010). "Mammalian Cell Transfection: The Present and The Future," *Anal Bioanal. Chem.* 397(8):3173-3178.

Kollias et al. (Jul. 4, 1986). "Regulated Expression Of Human $^{A}\gamma$-, β-, and Hybrid γβ-Globin Genes In Transgenic Mice: Manipulation Of The Developmental Expression Patterns," *Cell* 46:89-94.

Kozlowski, S. et al. (Aug. 7, 2006, e-pub. May 22, 2006). "Current and Future Issues In The Manufacturing and Development Of Monoclonal Antibodies," *Adv. Drug. Deliv. Rev.* 58(5-6):707-722.

Krumlauf, R. et al. (Jul. 1985). "Developmental Regulation Of α-Fetoprotein Genes In Transgenic Mice," *Mol. Cell. Biol.* 5(7):1639-1648.

Leder, A. et al. (May 23, 1986). "Consequences of Widespread Deregulation Of The c-myc Gene In Transgenic Mice: Multiple Neoplasms And Normal Development," *Cell* 45(4):485-495.

Li, F. et al. (Sep./Oct. 2010). "Cell Culture Processes For Monoclonal Antibody Production," *MAbs*, 2(5):466-477.

Lindmark, R. et al. (1983). "Binding Of Immunoglobulins To Protein A and Immunoglobulin Levels In Mammalian Sera," *J. Immunol. Meth.* 62:1-13.

Lu, C. et al. (Jan./Feb. 2013). "Characterization Of Monoclonal Antibody Size Variants Containing Extra Light Chains," *Mabs* 5(1):102-113.

Luo, J. et al. (2012, e-pub. Sep. 30, 2011). "Comparative Metabolite Analysis to Understand Lactate Metabolism Shift in Chinese Hamster Ovary Cell Culture Process," *Biotechnol Bioeng.* 109(1):146-156.

MacDonald, R.J. (1987). "Expression Of The Pancreatic Elastase I Gene In Transgenic Mice," *Hepatology* 7(1):42S-51S.

Magram, J. et al. (May 23, 1985). "Developmental Regulation Of A Cloned Adult β-Globin Gene In Transgenic Mice," *Nature* 315(6017):338-340.

Mason, A.J. et al. (Dec. 12, 1986). "The Hypogonadal Mouse: Reproductive Functions Restored By Gene Therapy," *Science* 234(4782):1372-1378.

McMahan, C.J. et al. (1991). "A Novel IL-1 Receptor, Cloned From B Cells by Mammalian Expression, Is Expressed In Many Cell Types," *EMBO J.* 10(10):2821-2832.

O'Keefe, E. (2013). "siRNAs and shRNAs: Tools For Protein Knockdown By Gene Silencing," *Materials & Methods* 3:197, 12 pages.

Ornitz, D.M. et al. (1985). "Elastase I Promoter Directs Expression Of Human Growth Hormone and SV40 T Antigen Genes To Pancreatic Acinar Cells In Transgenic Mice," *Cold Spring Harbor Symp. Quant. Biol.* 50:399-409.

Pinkert, C.A. et al. (1987). "An Albumin Enhancer Located 40 kb Upstream Functions Along With Its Promoter To Direct Efficient, Liver-Specific Expression In Transgenic Mice," *Genes and Devel.* 1:268-276.

Rao, D.D. et al. (2009, e-pub. Apr. 20, 2009). "siRNA vs. shRNA: Similarities and Differences," *Adv. Drug Deliv. Rev.* 61:746-759.

Rasmussen, B. et al. (1998). "Isolation, Characterization and Recombinant Protein Expression In Veggie-CHO: A Serum-Free CHO Host Cell Line," *Cytotechnology* 28:31-42.

(56) References Cited

OTHER PUBLICATIONS

Readhead, C. et al. (Feb. 27, 1987). "Expression Of A Myelin Basic Protein Gene In Transgenic Shiverer Mice: Correction Of The Dysmyelinating Phenotype," *Cell* 48(4):703-712.
Reynolds, A. et al. (Mar. 2004). "Rational siRNA Design For RNA Interference," *Nat. Biotechnol.* 22(3):326-330.
Reznik, S.E. et al. (2001). "Carboxypeptidases From A To Z: Implications In Embryonic Development and Wnt Binding," *Cell Mol. Life Sci.* 58(12-13):1790-1804.
Rules of siRNA design for RNA interference, Protocol Online, located at <http://www.protocol-online.org/prot/Protocols/Rules-of-siRNA-design-for-RNA-interferen . . . >, last visited Sep. 13, 2018, 1 page, (May 29, 2004).
Sambrook, J. et al. (1989). Molecular Cloning: A Laboratory Manual, 2nd ed., Cold Spring Harbor Laboratory, Cold Spring Harbor, NY Table Of Contents, 28 pages.
Shani, M. (Mar. 21, 1985). "Tissue-Specific Expression of Rat Myosin Light-Chain 2 Gene in Transgenic Mice," *Nature* 314(6008):283-286.
Sidhu, S.S. (May 2007). "Full-Length Antibodies On Display," *Nat. Biotechnol.* 25(5):537-538.
Silva, G. et al. (2011). "Meganucleases and Other Tools for Targeted Genome Engineering: Perspectives and Challenges for Gene Therapy," *Curr. Gene Ther.* 11:11-27.
Sreenivas, S. et al. (Feb. 1, 2016, e-pub. Oct. 22, 2015). "Disruption of KEX1 Gene Reduces The Proteolytic Degradation Of Secreted Two-Chain Insulin Glargine In Pichia Pastoris" *Protein Expression And Purification* 118:1-9.
Swift, G.H. et al. (Oct. 1984). "Tissue-Specific Expression Of The Rat Pancreatic Elastase I Gene In Transgenic Mice," *Cell* 38(3):639-646.
Tao J. et al. (Apr. 30, 2013). "SiRNA-targeted Carboxypeptidase D Inhibits Hepatocellular Carcinoma Growth," *Cell Biology International* 37(9):929-939).
Thomsen, D.R. et al. (Feb. 1984). "Promoter-Regulatory Region Of The Major Immediate Early Gene Of Human Cytomegalovirus," *Proc. Natl. Acad. USA* 81:659-663.
Urlaub, G. et al. (Jul. 1980). "Isolation Of Chinese Hamster Cell Mutants Deficient In Dihydrofolate Reductase Activity," *Proc. Natl. Acad. Sci. U.S.A.* 77(7):4216-4220.
Wagner, M.J. et al. (Mar. 1981). "Nucleotide Sequence Of The Thymidine Kinase Gene Of Herpes Simplex Virus Type 1," *Proc. Natl. Acad. Sci. USA* 78(3):1444-1445.
Xu, X. et al. (Aug. 2011, e-pub. Jul. 31, 2011). "The Genomic Sequence Of The Chinese Hamster Ovary (CHO)-K1 Cell Line," *Nat. Biotechnol.* 29(8):735-742.
Yamamoto, T. et al. (Dec. 1980). "Identification of A Functional Promoter In The Long Terminal Repeat Of Rous Sarcoma Virus," *Cell* 22(3):787-797.
International Preliminary Report on Patentability dated Mar. 27, 2018, for PCT Application No. PCT/US2016/052962, filed on Sep. 21, 2016, 6 pages.
International Search Report dated Dec. 13, 2016, for PCT Application No. PCT/US2016/052962, filed on Sep. 21, 2016, 5 pages.
Written Opinion dated Dec. 13, 2016, for PCT Application No. PCT/US2016/052962, filed on Sep. 21, 2016, 5 pages.
Boehm, T. et al. (May 1, 1999). "Disruption of the KEX1 Gene In Pichia Pastoris Allows Expression Of Full-Length Murine and Human Endostatin," Yeast 15(7):563-572.
DATABASE Entry No. P09620. (2005). "Pheromone-Processing Carboxypeptidase KEX1," 2 pages.
Jin, T. et al. (Sep. 2013, e-pub. Apr. 30, 2013). "SiRNA-Targeted Carboxypeptidase D Inhibits Hepatocellular Carcinoma Growth," Cell Biol. Int. 37(9):929-939.
Cooper, A. et al. (Jun. 1989). "Characterization of the Yeast KEX1 Gene Product: A carboxypeptidase Involved in Processing Secreted Precursor Proteins," Molecular and Cellular Biology 9(6):2706-2714.
Cai, B. et al. (Feb. 2011). "C-Terminal Lysine Processing Of Human Immunoglobulin G2 Heavy Chain In Vivo," Biotechnol Bioeng. 108(2):404-412.
Oshiro, G. et al. (2002). "Parallel identification of New Genes In *Saccharomyces cervisiae*," Genome Research 12:1210-1220.
Johnson, K.A. et al. (2007, e-pub. Oct. 30, 2006). "Cation Exchange-HPLC and Mass-Spectrometry Reveal C-Terminal Amidation of an IgG1 Heavy Chain," Analytical Biochemistry 360:75-33.

* cited by examiner

SEQUENCE LISTING

```
<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Synthetic construct

<400> SEQUENCE: 1

cccacacatt acaaatctta cca                                            23


<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
```

-continued

```
gagatttcga gggaccaaat                                                20


<210> SEQ ID NO 3
<211> LENGTH: 26
<212> TYPE: DNA
<213> ORGANISM: Artificial Sequence
<220> FEATURE:
<223> OTHER INFORMATION: Synthetic construct

<400> SEQUENCE: 3

ttgggacaga gtgctgagta tcgtca                                         26


<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4

gtgggatcaa tcacgatgtc                                                20


<210> SEQ ID NO 5
<211> LENGTH: 23
<212> TYPE: DNA
<213> ORGANISM: Artificial Sequence
<220> FEATURE:
<223> OTHER INFORMATION: Synthetic construct

<400> SEQUENCE: 5

ccttggcagt gacaatgtaa gta                                            23


<210> SEQ ID NO 6
<211> LENGTH: 25
<212> TYPE: DNA
<213> ORGANISM: Artificial Sequence
<220> FEATURE:
<223> OTHER INFORMATION: Synthetic construct

<400> SEQUENCE: 6

acatggggat tacttccgtc tgctg                                          25


<210> SEQ ID NO 7
<211> LENGTH: 25
<212> TYPE: DNA
<213> ORGANISM: Artificial Sequence
<220> FEATURE:
<223> OTHER INFORMATION: Synthetic construct

<400> SEQUENCE: 7

aacttggaga gtactacctg cttct                                          25


<210> SEQ ID NO 8
<211> LENGTH: 18
<212> TYPE: DNA
<213> ORGANISM: Artificial Sequence
<220> FEATURE:
<223> OTHER INFORMATION: Synthetic construct

<400> SEQUENCE: 8

tcatgcccag ggactgta                                                  18


<210> SEQ ID NO 9
<211> LENGTH: 25
<212> TYPE: DNA
```

<213> ORGANISM: Artificial Sequence
<220> FEATURE:
<223> OTHER INFORMATION: Synthetic construct

<400> SEQUENCE: 9
attgatcacg taggaccctg gcaaa 25

<210> SEQ ID NO 10
<211> LENGTH: 19
<212> TYPE: DNA
<213> ORGANISM: Artificial Sequence
<220> FEATURE:
<223> OTHER INFORMATION: Synthetic construct

<400> SEQUENCE: 10
tgaatgcgct ggtgaaagg 19

<210> SEQ ID NO 11
<211> LENGTH: 22
<212> TYPE: DNA
<213> ORGANISM: Artificial Sequence
<220> FEATURE:
<223> OTHER INFORMATION: Synthetic construct

<400> SEQUENCE: 11
tcctgggcca tatgtgtact tg 22

<210> SEQ ID NO 12
<211> LENGTH: 25
<212> TYPE: DNA
<213> ORGANISM: Artificial Sequence
<220> FEATURE:
<223> OTHER INFORMATION: Synthetic construct

<400> SEQUENCE: 12
cggtcaagga acttgcctct ctgca 25

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
tggctacctg gcaataacaa 20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
cgactccagc tcaaagtcaa 20

<210> SEQ ID NO 15
<211> LENGTH: 25
<212> TYPE: DNA
<213> ORGANISM: Artificial Sequence
<220> FEATURE:
<223> OTHER INFORMATION: Synthetic construct

<400> SEQUENCE: 15
aagtggcagt tcctttcaag cctgc 25

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
tcctctcagt ggtctgcttg g 21

<210> SEQ ID NO 17
<211> LENGTH: 22
<212> TYPE: DNA
<213> ORGANISM: Artificial Sequence
<220> FEATURE:
<223> OTHER INFORMATION: Synthetic construct

<400> SEQUENCE: 17
tggcgtgtgt agacttgcac tt 22

<210> SEQ ID NO 18
<211> LENGTH: 19
<212> TYPE: DNA
<213> ORGANISM: Artificial Sequence
<220> FEATURE:
<223> OTHER INFORMATION: Synthetic construct

<400> SEQUENCE: 18
tgccatccag cgtccccca 19

<210> SEQ ID NO 19
<211> LENGTH: 19
<212> TYPE: DNA
<213> ORGANISM: Artificial Sequence
<220> FEATURE:
<223> OTHER INFORMATION: Synthetic construct

<400> SEQUENCE: 19
ggaagagaac tgctactaa 19

<210> SEQ ID NO 20
<211> LENGTH: 19
<212> TYPE: DNA
<213> ORGANISM: Artificial Sequence
<220> FEATURE:
<223> OTHER INFORMATION: Synthetic construct

<400> SEQUENCE: 20
gaatggtgct tgatgagaa 19

<210> SEQ ID NO 21
<211> LENGTH: 23
<212> TYPE: DNA
<213> ORGANISM: Artificial Sequence
<220> FEATURE:
<223> OTHER INFORMATION: Synthetic construct

<400> SEQUENCE: 21
gaagacgaga ctttcaaaga cgg 23

<210> SEQ ID NO 22
<211> LENGTH: 23
<212> TYPE: DNA
<213> ORGANISM: Artificial Sequence
<220> FEATURE:

-continued

<223> OTHER INFORMATION: Synthetic construct

<400> SEQUENCE: 22
tcagttaggt ggcttaggtt cgg 23

<210> SEQ ID NO 23
<211> LENGTH: 25
<212> TYPE: DNA
<213> ORGANISM: Artificial Sequence
<220> FEATURE:
<223> OTHER INFORMATION: Synthetic construct

<400> SEQUENCE: 23
agttcattta tgaaagatcc tgtgg 25

<210> SEQ ID NO 24
<211> LENGTH: 24
<212> TYPE: DNA
<213> ORGANISM: Artificial Sequence
<220> FEATURE:
<223> OTHER INFORMATION: Synthetic construct

<400> SEQUENCE: 24
ggaaaggagt ccttcagtga acac 24

<210> SEQ ID NO 25
<211> LENGTH: 24
<212> TYPE: DNA
<213> ORGANISM: Artificial Sequence
<220> FEATURE:
<223> OTHER INFORMATION: Synthetic construct

<400> SEQUENCE: 25
ccagttctgc tgttacactt tgag 24

<210> SEQ ID NO 26
<211> LENGTH: 24
<212> TYPE: DNA
<213> ORGANISM: Artificial Sequence
<220> FEATURE:
<223> OTHER INFORMATION: Synthetic construct

<400> SEQUENCE: 26
aatgtttcct ctttcctgga cctt 24

EXPRESSION OF FC-CONTAINING PROTEINS

CROSS REFERENCE TO RELATED APPLICATIONS

This application is a U.S. national phase application under 35 U.S.C. § 371 of International Application No. PCT/US2016/052962, filed on Sep. 21, 2016, which claims priority to U.S. Provisional Patent Application No. 62/222,187, filed Sep. 22, 2015, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392032600SEQLIST.txt, date recorded: Mar. 21, 2018, size: 5,073 KB).

TECHNICAL FIELD

The present invention relates to compositions comprising a Fc-containing protein, wherein substantially all Fc-containing proteins have a C-terminal lysine on each Fc domain. The present invention further relates to host cells for producing said compositions, methods of making said host cells and compositions, and methods of use thereof.

BACKGROUND

Therapeutic Fc domain-containing proteins, e.g., monoclonal antibodies and Fc-containing fusion proteins, have emerged as important drugs for the treatment of diseases, such as cancer, autoimmune disease, and infection, and currently represent the fastest growing class of therapeutic agents. See, e.g., Beck et al., *Nat Rev Immunol,* 10, 2010. Clinically, polypeptide-based therapeutics have demonstrated potent activity due to their high degree of target specificity and ability to engage an immune response. See, e.g., Sidhu, *Nat Biotechnol,* 25, 2007. However, commercial production of a homogeneous polypeptide-based therapeutic is challenging as polypeptides are subject to numerous modifications, for example, different disulfide pairing, deamidation, oxidation, N-terminal glutamine cyclization, and different glycan structures. See, e.g., Carson, *Nat Biotechnol,* 23, 2005. Furthermore, the presence and structure consistency of polypeptide modifications are highly sensitive to production conditions. Inclusion of an immunoglobulin Fc domain with a biologically active polypeptide provides beneficial biological and pharmacological properties to the biologically active agent, including, increased plasma half-life allowing for prolonged therapeutic activity and less frequent dosing. See, Czajkowsky et al., *Mol Med,* 4, 2012. However, presence of a Fc domain further increases the potential for heterogeneity of a Fc-containing protein product, for example, variation of C-terminal lysine presence as compared across each Fc domain.

Industry standards for the production of biologics, such as Fc-containing proteins, require demonstration of product consistency across all clinical and commercial batches. Comparability studies of the polypeptide product must be conducted to ensure consistency following changes to production parameters, for example, those that occur during phase I to phase III production optimization, commercial scaling, and post-commercialization alterations. Production parameter changes include, but are not limited to, changes to the cell culture process parameters, cell culture media, host cell, purification, storage, and formulation. Furthermore, for multi-site production, it is necessary to ensure product consistency across all production facilities. Variability and heterogeneity in the levels of a polypeptide attribute, such as Fc domain C-terminal lysine presence, are considered to be an indication of a lack of production process control. See, Chirino et al., *Nat Biotechnol,* 22, 2004; and Kozlowski et al., *J Pharm Sci,* 97, 2006. Differences in cell lines and their sensitivity to manufacturing processes, e.g., culture conditions, affect characteristics of the final product. For example, Fc domain C-terminal lysine processing, i.e., cleavage, during production of a monoclonal antibody (consisting of two heavy chains), results in a mixture of antibody isoforms bearing zero, one, or two Fc domain C-terminal lysine residues. Extensive Fc domain C-terminal lysine processing can be observed in the production of an antibody, resulting in large percentages of the total antibody population bearing zero or one Fc domain C-terminal lysine. See, Dick et al., *Biotechnol Bioeng,* 100, 2008. Thus, the heterogeneity of Fc domain C-terminal lysine presence presents a unique challenge in the production of therapeutic Fc-containing proteins.

Extensive cell culture condition optimization has been investigated to decrease the heterogeneity of Fc domain C-terminal lysine presence that results during the production of Fc-containing proteins. For example, the effects of controlling cell media concentrations of heavy metals, such as zinc, cell media concentrations of amino acids, pH, and temperature on antibody Fc domain C-terminal lysine presence has been described in U.S. Patent Application No. 20130280274. However, as demonstrated in U.S. Patent Application No. 20130280274, optimization of cell culture parameters does not eliminate the heterogeneity of Fc domain C-terminal lysine presence.

Fc domains of IgG1, IgG2, and IgG4 isotype immunoglobulins contain a conserved basic amino acid lysine at the C-terminus of each Fc domain. Heterogeneity of Fc domain C-terminal lysine presence of these immunoglobulin isotypes is believed to result from proteolysis by endogenous carboxypeptidase(s) during cell culture production. See, Harris, *J Chromatogr A,* 705, 1995; and Luo et al., *Biotechnol Bioeng,* 109, 2012. Carboxypeptidases are enzymes that hydrolytically cleave amino acids from the C-termini of proteins and peptides. There are 13 known members of carboxypeptidases found in most mammalian species. See, Reznik et al., *Cell Mol Life Sci,* 58, 2001. While different carboxypeptidase proteins and their activities have been detected in CHO cells, a commonly used production host cell, it is not known which carboxypeptidase(s) is responsible for the removal of the Fc domain C-terminal lysine. See, Dick et al., *Biotechnol Bioeng,* 100, 2008. It has previously been speculated that one or more carboxypeptidases, including CpB and CpM, may be involved in Fc domain C-terminal lysine processing. See, Dick et al., *Biotechnol Bioeng,* 100, 2008; Harris, *J Chromatogr A,* 705, 1995; and Luo et al., *Biotechnol Bioeng,* 109, 2012.

The disclosures of all publications, patents, patent applications and published patent applications referred to herein are hereby incorporated herein by reference in their entirety.

BRIEF SUMMARY OF THE INVENTION

Provided herein are host cells for expression of a Fc-containing protein, wherein the host cell has at least a 60% reduction of a carboxypeptidase D (CpD) expression level as compared to a host cell comprising a wild type CpD gene without CpD gene inactivation.

In some embodiments according to (or as applied to) any of the embodiments above, the host cell is a eukaryotic cell. In some embodiments, the host cell is a mammalian cell. In some embodiments, the host cell is a Chinese hamster ovary (CHO) cell.

In some embodiments according to (or as applied to) any of the embodiments above, the Fc-containing protein is an antibody. In some embodiments, the antibody is a monoclonal antibody.

In some embodiments according to (or as applied to) any of the embodiments above, the Fc-containing protein is a Fc-containing fusion protein.

In some embodiments according to (or as applied to) any of the embodiments above, the CpD gene in the host cell is inactivated. In some embodiments, the CpD gene is inactivated by siRNA. In some embodiments, the CpD gene is inactivated by shRNA. In some embodiments, the CpD gene is inactivated by gene deletion. In some embodiments, the CpD gene is inactivated by gene addition or substitution. In some embodiments, the CpD gene is inactivated using a clustered, regularly interspaced, short palindromic repeats (CRISPR) system. In some embodiments, the CpD gene is inactivated using a transcription activator-like effector nuclease (TALEN) system. In some embodiments, the CpD gene is inactivated using a zinc-finger nuclease (ZFN) system. In some embodiments, the CpD gene is inactivated using a meganuclease system.

In some embodiments according to (or as applied to) any of the embodiments above, the host cell comprises an expression vector comprising a nucleic acid encoding the Fc-containing protein.

Provided herein are cell culture systems comprising a host cell of any of the embodiments above.

Provided herein are methods of producing a host cell, wherein the methods comprise inactivating the CpD gene in the host cell, thereby producing the host cell of any of the embodiments above.

In some embodiments, the method of producing a host cell comprises inactivating the CpD gene using a siRNA system. In some embodiments, the method of producing a host cell comprises inactivating the CpD gene using a shRNA system. In some embodiments, the method of producing a host cell comprises inactivating the CpD gene by gene deletion. In some embodiments, the method of producing a host cell comprises inactivating the CpD gene by gene addition or substitution. In some embodiments, the method of producing a host cell comprises inactivating the CpD gene using a CRISPR system. In some embodiments, the method of producing a host cell comprises inactivating the CpD gene using a TALEN system. In some embodiments, the method of producing a host cell comprises inactivating the CpD gene using a ZFN system. In some embodiments, the method of producing a host cell comprises inactivating the CpD gene using a meganuclease system.

Provided herein are methods of making a Fc-containing protein comprising: a) culturing a host cell, and b) obtaining the Fc-containing protein expressed by the host cell.

Provided herein are compositions comprising a plurality of Fc-containing proteins, wherein substantially all Fc-containing proteins in the composition have a C-terminal lysine on each Fc domain. In some embodiments, substantially all Fc-containing proteins of the composition have the same amino acid sequence. In some embodiments, the plurality of Fc-containing proteins are substantially homogeneous in charge state. In some embodiments, the Fc-containing protein is a Fc-containing fusion protein. In some embodiments, the Fc-containing protein is an antibody. In some embodiments, the antibody is a human antibody. In some embodiments, the antibody is a humanized antibody. In some embodiments, the antibody comprises two heavy chains, and wherein each heavy chain comprises a C-terminal lysine. In some embodiments, the Fc-containing protein is conjugated to a drug. In some embodiments, the Fc-containing proteins in the composition comprise an IgG1 Fc domain. In some embodiments, the Fc-containing proteins in the composition comprise an IgG2 Fc domain. In some embodiments, the Fc-containing proteins in the composition comprise an IgG4 Fc domain.

In some embodiments according to (or as applied to) any of the embodiments above, the composition comprising a plurality of Fc-containing proteins is a pharmaceutical composition. In some embodiments, the pharmaceutical composition comprising a plurality of Fc-containing proteins is a sterile pharmaceutical composition.

In some embodiments according to (or as applied to) any of the embodiments above, the composition comprising a plurality of Fc-containing proteins is a cell culture medium.

In some embodiments according to (or as applied to) any of the embodiments above, the composition comprising a plurality of Fc-containing proteins is a cell lysate.

In some embodiments according to (or as applied to) any of the embodiments above, the composition comprising a plurality of Fc-containing proteins is an eluate from a protein purification column.

Also provided herein are methods of treating a disease in an individual in need thereof comprising administering to the individual a pharmaceutical composition or a sterile pharmaceutical composition described in the embodiments above. In some embodiments, the method of treating a disease in an individual in need thereof comprises administering the composition parenterally. In some embodiments, the method of treating a disease in an individual in need thereof comprises administering the composition intravenously or subcutaneously. In some embodiments, the method of treating a disease in an individual in need thereof comprises administering the composition locally. In some embodiments, the method of treating a disease in an individual in need thereof comprises administering the composition topically.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE FIGURES

FIG. 1A shows relative carboxypeptidase B (CpB), carboxypeptidase E (CpE), carboxypeptidase M (CpM), carboxypeptidase N1 (CpN1), and carboxypeptidase D (CpD) mRNA expression levels in DP12 and CHOK1 host cells. Expression levels of mRNA for each carboxypeptidase were normalized to the housekeeping gene β-2-microglobulin (b2m). White bars represent measurements from the DP12 host and black bars represent measurements from the CHOK1 host. FIG. 1B shows relative carboxypeptidase mRNA expression levels in antibody-expressing cell lines. Expression level of mRNA for each carboxypeptidase was normalized to the house keeping gene b2m. White bars represent measurements from the antibody-expressing cell line A and black bars represent measurements from the antibody-expressing cell line B.

FIG. 2A shows relative CpD mRNA expression levels in antibody-expressing cell line A and antibody-expressing cell line B. The grey bars represent the CpD mRNA level in the cell lines after scramble construct transfection for both cell line A and cell line B; the white bar represents the CpD mRNA level in cell line A after CpDi construct transfection; and the black bar represents CpD mRNA in cell line B after CpDi construct transfection. The expression level of CpD mRNA in each cell line was compared to the expression level of CpD in the respective cell line following transfection with a scramble construct.

FIG. 2B shows relative CpN mRNA expression levels in antibody-expressing cell line A and antibody-expressing cell line B. The grey bars represent the mRNA level in the cell lines after scramble construct transfection; the white bar represents the mRNA level in cell line A after CpNi construct transfection; and the black bar represents mRNA level in cell line B after CpNi construct transfection. The expression level of CpN mRNA in each cell line was compared to the expression level of CpN in the respective cell line following transfection with a scramble construct.

FIG. 4A shows a schematic diagram of the wild type CpD allele. Two guide RNA (gRNA) sequences (gRNA 1 and gRNA 2) were used for targeting exon 2 and exon 21 of the CHO CpD gene, respectively, for gene knockout via CRISPR. The distance between the two gRNAs is about 46 kb. Forward and reverse PCR primers used to detect the WT CpD sequence aimed to be removed by CRISPR are denoted as WT.F and WT.R, respectively. FIG. 4B shows a schematic diagram of the KO CpD allele. Forward and reverse PCR primers used to detect the KO CpD allele are denoted as KO.F and KO.R, respectively.

FIG. 5A shows CpD RNA expression levels of two CpD KO clones and two CpD WT clones. FIG. 5B shows Western blot analysis of two CpD KO clones and two CpD WT clones.

FIG. 6A shows the titer of expressed antibody at day 14. FIG. 6B shows the specific productivity (Qp) in picograms (pg) per cell per day. FIG. 6C shows integrated viable cell counts in 100 millions of cells-days per liter after 14 days of culture.

DETAILED DESCRIPTION OF THE INVENTION

Figure 1A:
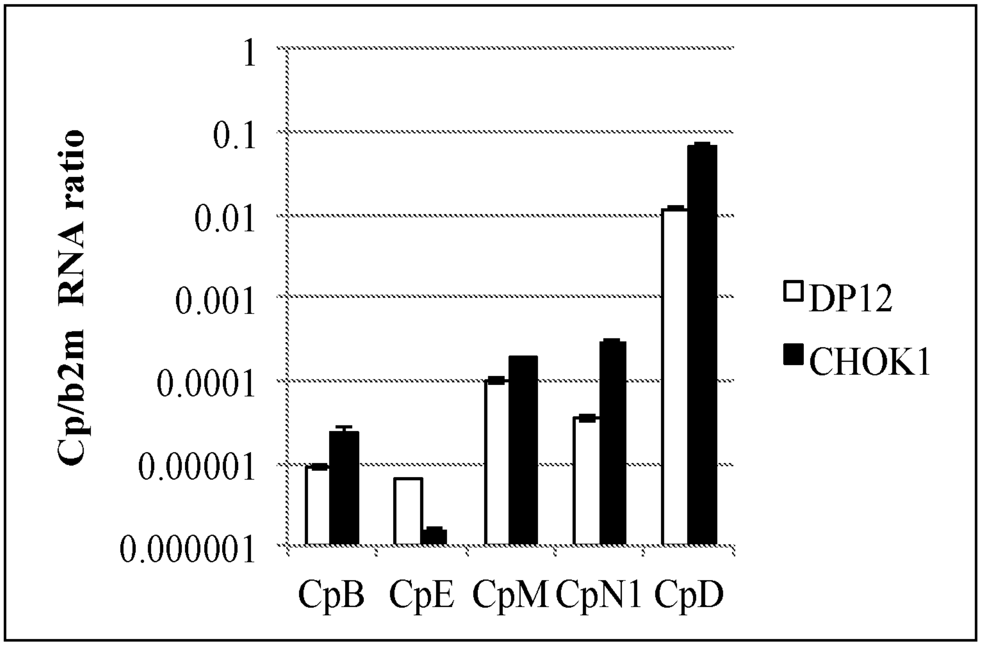
FIGS. 1A-1B shows qPCR mRNA analysis of endogenous carboxypeptidases in cell lines. Each error bar denotes 1 standard deviation.

The present application is based on the surprising finding that carboxypeptidase D (CpD), a zinc-binding enzyme that hydrolyzes single C-terminal amino acids of proteins, is the sole carboxypeptidase responsible for Fc domain C-terminal lysine processing (i.e., cleavage). Specifically, using mass spectrometry analysis, we showed that Fc domain C-terminal lysine cleavage was completely abolished in CpD knockout cells, thus demonstrating that CpD is the only endogenous carboxypeptidase that cleaves antibody Fc domain C-terminal lysines in CHO cells.

The present application thus provides a method of producing Fc-containing proteins with a C-terminal lysine on each Fc domain by using a host cell that has a reduced level of CpD expression. The products produced by such methods can lead to 100% homogeneity in Fc domain C-terminal lysine presence. Such a method eliminates the need to consider the effects of changing production conditions on the status of Fc domain C-terminal lysine presence, and thus greatly facilitates the manufacturing process of Fc-containing proteins. For example, use of such a method for the production of a Fc-containing protein eliminates the need to optimize cell culture conditions to minimize variability of Fc domain C-terminal lysine presence as compared across a plurality of production batches (e.g., comparison of a plurality of clinical and commercial batches). Additionally, for example, use of such a method for the production of a Fc-containing protein eliminates the need to optimize cell culture conditions to balance minimizing the variability of Fc domain C-terminal lysine presence with the variability and status of other characteristics of the Fc-containing protein (e.g., titer of Fc-containing protein and presence of post-translational modifications). Furthermore, such a method of producing Fc-containing proteins greatly facilitates the subsequent analysis of the Fc-containing proteins. For example, use of such a method for the production of a Fc-containing protein eliminates the need to incorporate additional steps to assay for charge variants of a plurality of Fc-containing proteins with heterogeneous Fc domain C-terminal lysine presence (such as, e.g., a step involving incubation with CpB to remove all Fc domain C-terminal lysines).

Furthermore, retention of the Fc domain C-terminal lysine can inhibit subsequent alterations of Fc domain C-terminal amino acids during Fc-containing protein production. For example, the conserved Fc domain C-terminal amino acid sequence of IgG1, IgG2, and IgG3 immunoglobulins is proline-glycine-lysine. Cleavage of the Fc domain C-terminal lysine generates a terminal glycine, allowing peptidylglycine α-amidating monooxygenase to catalyze a two-step amidation reaction to remove the glycine residue and add an amide moiety to the proline in IgG1, IgG2, and IgG3 (activity of this enzyme is also dependent on the copper concentration in the culture media). Fc domain C-terminal proline amidation, and the extent thereof, can further generate charge variants within a population of Fc-containing proteins.

Thus, the present application, in one aspect provides a host cell for expression of a Fc-containing protein, wherein the host cell has a reduced level of carboxypeptidase D (CpD) expression. The present application, in another aspect, provides a cell culture system comprising the host cell. The present application, in yet another aspect, provides a method of producing a host cell, wherein the method comprises inactivating the CpD gene in the host cell, thereby producing the host cell. The present application, in yet another aspect, provides a method of making a Fc-containing protein comprising culturing the host cell and obtaining the Fc-containing protein expressed by the host cell. The present application, in yet another aspect, provides a composition comprising a plurality of Fc-containing proteins, wherein substantially all Fc-containing proteins in the composition have a C-terminal lysine on each Fc domain. The present application, in yet another aspect, provides a method of treating a disease in an individual in need thereof comprising administering to the individual the composition, wherein the composition is a pharmaceutical composition comprising a plurality of Fc-containing proteins having a C-terminal lysine on each Fc domain.

Definitions

"Fc domain," as used herein, refers to a Fc region of an immunoglobulin heavy chain or a C-terminal fragment thereof. The term includes wild type Fc domains and variant Fc domains. In some embodiments, the human IgG heavy chain Fc domain extends from Cys226, or from Pro230, to the carboxyl-terminus of the heavy chain (amino acid number is according to the EU numbering system, also called the EU index, as described in Kabat et al., *Sequences of Proteins of Immunological Interest,* 5th Ed. Public Health Service, National Institutes of Health, Bethesda, Md., 1991). In some embodiments, the term includes a C-terminal fragment of an immunoglobulin heavy chain and one or more constant regions. In some embodiments, for IgG, the Fc domain may comprise immunoglobulin domains CH2 and CH3 and the hinge between CH1 and CH2.

"Fc-containing protein," as used herein, refers to a protein (e.g., an antibody or a Fc-containing fusion protein) comprising a Fc domain. In some embodiments, the Fc-containing protein comprises one or more protein subunits. In some embodiments, the Fc-containing protein comprises one or more polypeptides.

As used herein, "Fc-containing fusion protein" refers to a protein comprising a Fc domain fused to at least one other heterologous protein unit or polypeptide.

The term "polypeptide" used herein refers to a single polypeptide chain.

The term "heavy chain" used herein refers to an immunoglobulin heavy chain.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they comprise a Fc domain.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., $C_H2$ and/or $C_H3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

"Host cell," as used herein, refers to a cell capable of producing a protein or polypeptide product. For example, a host cell can produce a Fc-containing protein.

The term "individual" refers to a mammal and includes, but is not limited to, human, bovine, horse, feline, canine, rodent, or primate.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The methods of the invention contemplate any one or more of these aspects of treatment.

A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically, but not necessarily, since a prophylactic dose is used in subjects prior to or at the earlier stage of disease, the prophylactically effective amount can be less than the therapeutically effective amount.

It is understood that aspects and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X."

As used herein and in the appended claims, the singular forms "a," "or," and "the" include plural referents unless the context clearly dictates otherwise.

Host Cell

The present application provides a host cell for expression of a Fc-containing protein, wherein the host cell has a reduced level of carboxypeptidase D (CpD) expression.

Among the host cells that may be employed are eukaryotic cells, such as yeast or higher eukaryotic cells. Higher eukaryotic cells include insect cells and established cell lines of mammalian origin.

Examples of suitable mammalian host cell include the COS-7 line of monkey kidney cells (ATCC CRL 1651) (Gluzman et al., *Cell,* 23, 1981), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., *Cytotechnology,* 28, 1998), HeLa cells, BHK (ATCC CRL10) cell lines, and the CVI/EBNA cell line derived from the African green monkey kidney cell line CVI (ATCC CCL 70) as described by McMahan et al., *EMBO J,* 10, 1991, human embryonic kidney cells such as 293, 293 EBNA, or MSR 293, human epidermal A431 cells, human Colo205 cells, other transformed primate cell lines, normal diploid cells, cell strains derived from in vitro culture of primary tissue, primary explants, HL-60, U937, HaK, or Jurkat cells. Optionally, for example, mammalian cell lines such as HepG2/3B, KB, NIH 3T3 or S49, can be used as host cells.

In some embodiments, the host cell is a CHO cell. CHO cells are well known in the art. See, e.g., Xu et al., *Nat Biotechnol,* 29, 2011. In some embodiments, the host cell is a DP12 host cell. In some embodiments, the host cell is a DUXB-11 derived DHFR-deficient DP12 host cell. In some embodiments, the host cell is a CHOK1 host cell. In some embodiments, the host cell is a DHFR-positive CHOK1 host cell. In some embodiments, the host cell is a CHOK1M host cell.

In some embodiments, the host cell is a mouse host cell. In some embodiments, the host cell is a Sp2/0 host cell. In some embodiments, the host cell is a NS0 host cell.

In some embodiments, the host cell is a hybridoma. In some embodiments, the hybridoma is an antibody-producing cell, wherein the antibody-producing cell is collected from a host following immunization of the host with an antigen. In some embodiments, the antibody-producing cell is fused with a myeloma cell. In some embodiments, the host cell is a mouse myeloma-derived cell line.

Alternatively, the host cell can be a lower eukaryote such as yeast. Suitable yeasts include *Saccharomyces cerevisiae, Schizosaccharomyces pombe, Kluyveromyces* strains, Candida, or any yeast strain capable of expressing heterologous polypeptides.

As used herein, "a reduced level of CpD expression," refers to an at least 60% reduction of a CpD expression level, as compared to a host cell comprising a wild type CpD gene without CpD gene inactivation. In some embodiments, the host cell has at least a 60% reduction of a CpD expression level, as compared to a host cell prior to inactivation. In some embodiments, the CpD expression level is reduced by at least about 60%, 65%, 70%, 75%, 80%, 85%, 90%, 95%, or 100%. In some embodiments, the CpD expression level is reduced by at least 95%. In some embodiments, the CpD expression level is reduced by 100%. In some embodiments, the CpD expression level is reduced by about 60% to 100%, about 70% to 100%, about 80% to 100%, about 90% to 100%, or about 95% to 100%.

In some embodiments, the CpD gene in the host cell is inactivated, wherein the reduction of a CpD expression level is based on a DNA level. In some embodiments, the CpD gene in the host cell is inactivated, wherein the reduction of a CpD expression level is based on a RNA level. In some embodiments, the CpD gene in the host cell is inactivated, wherein the reduction of a CpD expression level is based on a polypeptide level.

In some embodiments, the CpD gene in the host cell is inactivated, wherein the reduced expression level is based on a CpD expression level following gene inactivation. In some embodiments, the CpD gene in the host cell is inactivated, wherein the reduced expression level is based on a DNA level. In some embodiments, the CpD gene in the host cell is inactivated, wherein the reduced expression level is based on a RNA level. In some embodiments, the CpD gene in the host cell is inactivated, wherein the reduced expression level is based on a polypeptide level.

In some embodiments, the CpD gene in the host cell is inactivated, wherein the CpD expression level is reduced by at least 60%. In some embodiments, the CpD gene in the host cell is inactivated, wherein the CpD expression level is reduced by at least 90%. In some embodiments, the CpD gene in the host cell is inactivated, wherein the CpD expression level is reduced by at least 95%. In some embodiments, the CpD gene in the host cell is inactivated, wherein the CpD expression level is reduced by 100%.

In some embodiments, the CpD gene in the host cell is inactivated. As used herein, "inactivated" refers to inhibiting the translation, or potential future translation, of a gene (i.e., expression of a protein). Inactivation can occur at any stage or process of gene expression, including, but not limited to, transcription, translation, and protein expression, and inactivation can affect any gene or gene product including, but not limited to, DNA, RNA, such as mRNA, and polypeptides.

Methods and techniques for inactivating the CpD gene in a host cell include, but are not limited to, small interfering RNA (siRNA), small hairpin RNA (shRNA; also referred to as a short hairpin RNA), clustered, regularly interspaced, short palindromic repeats (CRISPR), transcription activator-like effector nuclease (TALEN), zinc-finger nuclease (ZFN), homologous recombination, non-homologous end-joining, and meganuclease. See, e.g., O'Keefe, *Mater Methods,* 3, 2013; Doench et al., *Nat Biotechnol,* 32, 2014; Gaj et al., *Trends Biotechnol,* 31, 2014; and Silva et al., *Curr Gene Ther,* 11, 2011.

In some embodiments, the CpD gene is inactivated by a small interfering RNA (siRNA) system. Methods for identifying siRNA sequences suitable for CpD gene inactivation are well known in the art. For example, general consideration for developing and identifying siRNA to target the CpD gene include: a) first search sequences that are preferably 21-23 nucleotides in length (followed by reduction of sequence length as necessary), b) avoid regions within 50-100 base pairs of the start codon and the termination codon, c) avoid intron regions, d) avoid stretches of four or more bases, e.g., AAAA, e) avoid regions with GC content that is less than 30% or greater than 60%, f) avoid repeats and low sequence complexity, g) avoid single nucleotide polymorphism sites, and h) avoid sequences that are complementary to sequences in other off-target genes. See, e.g., *Rules of siRNA design for RNA interference*, Protocol Online, May 29, 2004; and Reynolds et al., *Nat Biotechnol,* 22, 2004.

In some embodiments, the siRNA system comprises a siRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the siRNA nucleotide sequence is approximately 10-25 nucleotides in length. In some embodiments, the siRNA nucleotide sequence is approximately 15-25 nucleotides in length. In some embodiments, the siRNA nucleotide sequence is at least about 10, at least about 15, at least about 20, or at least about 25 nucleotides in length. In some embodiments, the siRNA system comprises a nucleotide sequence that is at least about 80%, at least about 85%, at least about 90%, at least about 95%, or 100% complementary to a region of a CpD mRNA molecule. In some embodiments, the siRNA system comprises a nucleotide sequence that is at least at least about 80%, at least about 85%, at least about 90%, at least about 95%, or 100% complementary to a region of a CpD pro-mRNA molecule. In some, embodiments, the siRNA system comprises a double stranded RNA molecule. In some embodiments, the siRNA system comprises a single stranded RNA molecule. In some embodiments, the host cell comprises a siRNA system as described in the any of the embodiments herein. In some embodiments, the host cell comprises a pro-siRNA nucleotide sequence that is processed into an active siRNA molecule as described in the any of the embodiments herein. In some embodiments, the host cell comprises a siRNA nucleotide sequence that is at least about 80%, at least about 85%, at least about 90%, at least about 95%, or 100% complementary to a region of a CpD mRNA molecule. In some embodiments, the host cell comprises an expression vector encoding a siRNA molecule as described in the any of the embodiments herein. In some embodiments, the host cell comprises an expression vector encoding a pro-siRNA molecule as described in the any of the embodiments herein.

In some embodiments, the siRNA system comprises a delivery vector. In some embodiments, the host cell comprises a delivery vector. In some embodiments, the delivery vector comprises the pro-siRNA and/or siRNA molecule.

Exemplary CpD siRNA target sequences are listed in Table 1.

TABLE 1

Exemplary CpD siRNA target sequences siRNA.

| SEQ ID NO.: | CpD siRNA nucleotide sequence: |
|---|---|
| 19 | GGA AGA GAA CTG CTA CTA A |

In some embodiments, the CpD gene is inactivated by a small hairpin RNA (shRNA; also referred to as a short hairpin RNA) system. Gene inactivation by shRNA systems are well known in the art. In some embodiments, the shRNA system comprises a nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the shRNA nucleotide sequence is approximately 10-25 nucleotides in length. In some embodiments, the shRNA nucleotide sequence is approximately 15-25 nucleotides in length. In some embodiments, the shRNA nucleotide sequence is at least about 10, at least about 15, at least about 20, or at least about 25 nucleotides in length. In some embodiments, the shRNA system comprises a nucleotide sequence that is at least about 80%, at least about 85%, at least about 90%, at least about 95%, or 100% complementary to a region of a CpD mRNA molecule. In some embodiments, the shRNA system comprises a nucleotide sequence that is at least about 80%, at least about 85%, at least about 90%, at least about 95%, or 100% complementary to a region of a CpD pro-mRNA molecule. In some, embodiments, the shRNA system comprises a double stranded RNA molecule. In some embodiments, the shRNA system comprises a single stranded RNA molecule. In some embodiments, the host cell comprises a shRNA system as described in the any of the embodiments herein. In some embodiments, the host cell comprises a pre-shRNA nucleotide sequence that is processed in an active shRNA nucleotide sequence as described in any of the embodiments herein. In some embodiments, the pro-shRNA molecule composed of DNA. In some embodiments, the pro-shRNA molecule is a DNA construct. In some embodiments, the host cell comprises a shRNA nucleotide sequence that is at least about 80%, at least about 85%, at least about 90%, at least about 95%, or 100% complementary to a region of a CpD mRNA molecule. In some embodiments, the host cell comprises an expression vector encoding a shRNA molecule as described in the any of the embodiments herein. In some embodiments, the host cell comprises an expression vector encoding a pro-shRNA molecule as described in the any of the embodiments herein.

In some embodiments, the shRNA system comprises a delivery vector. In some embodiments, the host comprises a delivery vector. In some embodiments, the delivery vector comprises the pro-shRNA and/or shRNA molecule.

In some embodiments, the CpD gene is inactivated by a gene deletion. As used herein, "gene deletion" refers to removal of at least a portion of a DNA sequence from, or in proximity to, a gene. In some embodiments, the sequence subjected to gene deletion comprises an exonic sequence of a gene. In some embodiments, the sequence subjected to gene deletion comprises a promoter sequence of a gene. In some embodiments, the sequence subjected to gene deletion comprises a flanking sequence of a gene. In some embodiments, a portion of a gene sequence is removed from a gene. In some embodiments, a portion of the CpD gene sequence is removed from, or in proximity to, the CpD gene. In some embodiments, the complete gene sequence is removed from a chromosome. In some embodiments, the complete CpD sequence is removed from a chromosome. In some embodiments, the host cell comprises a gene deletion as described in the any of the embodiments herein. In some embodiments, the host cell comprises a gene deletion in the CpD gene. In some embodiments, the host cell comprises a gene deletion in proximity to the CpD gene.

In some embodiments, the CpD gene is inactivated by a gene addition or substitution. As used herein, "gene addition" or "gene substitution" refers to an alteration of a gene sequence, including insertion or substitution of one or more nucleotides or nucleotide base pairs. In some embodiments, the intronic sequence of the gene is altered. In some embodiments, the exonic sequence of the gene is altered. In some embodiments, the promoter sequence of the gene is altered. In some embodiments, the flanking sequence of the gene is altered. In some embodiments, one nucleotide or nucleotide base pair is added to a gene sequence. In some embodiments, at least one consecutive nucleotide or nucleotide base pair is added to a gene sequence. In some embodiments, the host cell comprises a gene addition or substitution as described in the any of the embodiments herein. In some embodiments, the host cell comprises a gene addition or substitution in the CpD gene.

In some embodiments, the CpD gene is inactivated by a gene deletion, wherein deletion of at least one nucleotide or nucleotide base pair in a gene sequence results in a non-functional gene product. In some embodiments, the CpD gene is inactivated by a gene deletion, wherein deletion of at least one nucleotide to a gene sequence results in a gene product that no longer has the original gene product function or activity. In some embodiments, the CpD gene is inactivated by a gene deletion, wherein deletion of at least one nucleotide to a gene sequence results in a dysfunctional gene product.

In some embodiments, the CpD gene is inactivated by a gene addition or substitution, wherein addition or substitution of at least one nucleotide or nucleotide base pair into the CpD gene sequence results in a non-functional gene product. In some embodiments, the CpD gene is inactivated by a gene inactivation, wherein incorporation or substitution of at least one nucleotide to the CpD gene sequence results in a gene product that no longer has the original gene product function or activity. In some embodiments, the CpD gene is inactivated by a gene addition or substitution, wherein incorporation or substitution of at least one nucleotide into the CpD gene sequence results in a dysfunctional gene product.

In some embodiments, the host cell comprises a non-functional CpD gene product. In some embodiments, the host cell comprises a CpD gene product that does not have the original CpD gene product function or activity. In some embodiments, the host cell comprises a dysfunctional CpD gene product.

In some embodiments, the host cell comprises an inactivated CpD gene, wherein the inactivated CpD gene will not express a full length, and functional, CpD gene product (e.g., a full length CpD polypeptide sequence). In some embodiments, the host cell comprises an inactivated CpD gene, wherein the inactivated CpD gene will not express an endogenous CpD gene product sequence. In some embodiments, the host cell comprises an inactivated CpD gene, wherein the inactivated CpD gene will express a variant CpD gene product. In some embodiments, the host cell comprises a variant CpD gene product.

In some embodiments, the host cell comprises a delivery vector. In some embodiments, the delivery vector is a virus vector. In some embodiments, the delivery vector is a lentivirus. In some embodiments, the delivery vector is an adenovirus. In some embodiments, the vector comprises a promoter.

In some embodiments, the host cell is a stable knockdown host cell. In some embodiments, the host cell is a stable CpD knockdown cell line. In some embodiments, the host cell is a transient knockdown cell line. In some embodiments, the host cell is a transient CpD knockdown cell line.

In some embodiments, the host cell further comprises an inactivated gene other than CpD.

In general, host cells are transformed with a recombinant expression vector that comprises DNA encoding a desired Fc-containing protein. Additionally, the host cells of the present application can be a blank host cell. As used herein, "blank host" refers to a cell that does not contain an expression vector encoding a Fc-containing protein. In some embodiments, the blank host cell is a CHO cell. In some embodiments, the blank host cell is a mouse cell.

Also provided by the present application are host cells comprising nucleic acids encoding Fc-containing proteins described herein. Nucleic acid molecules provided by the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids provided herein are preferentially derived from human sources.

As noted elsewhere herein, an "isolated" nucleic acid is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct.

In certain embodiments, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or intrans, that are typically present in eukaryotic genes. Sequences of nontranslated DNA can be present 5' or 3' from an open reading frame, where the same do not interfere with manipulation or expression of the coding region.

In some embodiments, the host cell is capable of expressing a Fc-containing protein. In some embodiments, the host cell comprises a Fc-containing protein. In some embodiments, the host cell is capable of secreting a Fc-containing protein.

In some embodiments, the host cell is capable of expressing a Fc-containing protein at a similar output rate of the host cell prior to CpD gene inactivation. In some embodiments, the host cell is capable of expressing a Fc-containing protein at the same output rate of the host cell prior to CpD gene inactivation. In some embodiments, the host cell is capable of expressing a Fc-containing protein at about 70%, 75%, 80%, 85%, 90%, 95%, or 100% of the output rate of the host cell prior to CpD gene inactivation.

In some embodiments, the host cell further comprises a gene modification. Optimization of a host cell for the purposes of producing a Fc-containing protein via gene modification is well known in the art and includes considerations pertaining to, for example, glycosylation patterns, vector selection properties for integration methods, and any other cellular property that would be desirable to manipulate for the production of a Fc-containing protein. In some embodiments, the gene modification is a targeted gene modification. In some embodiments, the gene modification is a knockout gene modification. In some embodiments, the gene modification is a knock-in gene modification.

Fc-Containing Protein

The present application provides a Fc-containing protein, wherein each Fc domain of the Fc-containing protein has a C-terminal lysine.

In some embodiments, the Fc-containing protein comprises a Fc domain. In some embodiments, the Fc-containing protein comprises one or more Fc domains. In some embodiments, the Fc-containing protein comprises two Fc domains.

In some embodiments, the Fc-containing protein comprises a heavy chain. In some embodiments, the Fc-containing protein comprises at least one heavy chain. In some embodiments, the Fc-containing protein comprises one or more heavy chains. In some embodiments, the Fc-containing protein comprises two heavy chains.

In some embodiments, the Fc-containing protein comprises a Fc domain, wherein the Fc domain comprises a C-terminal lysine. In some embodiments, the Fc-containing protein comprises at least one Fc domain, wherein each Fc domain comprises a C-terminal lysine. In some embodiments, the Fc-containing protein comprises one or more Fc domain, wherein each Fc domain comprises a C-terminal lysine. In some embodiments, the Fc-containing protein comprises two Fc domains, wherein each Fc domain comprises a C-terminal lysine.

In some embodiments, the Fc-containing protein comprises a heavy chain, wherein the heavy chain comprises a C-terminal lysine. In some embodiments, the Fc-containing protein comprises at least one heavy chain, wherein each heavy chain comprises a C-terminal lysine. In some embodiments, the Fc-containing protein comprises one or more heavy chains, wherein each heavy chain comprises a C-terminal lysine. In some embodiments, the Fc-containing protein comprises two heavy chains, wherein each heavy chain comprises a C-terminal lysine.

In some embodiments, the Fc-containing protein is a multimeric protein.

In some embodiments, the Fc-containing protein is an antibody. In some embodiments, the antibody is a human antibody. In some embodiments, the antibody is a humanized antibody. In some embodiments, the antibody is a monoclonal antibody. In some embodiments, the antibody is a chimeric antibody. In some embodiments, the antibody is a bispecific antibody. In some embodiments, the antibody is a multispecific antibody.

In some embodiments, the Fc-containing protein is a Fc-containing fusion protein. In some embodiments, the Fc-containing fusion protein comprises one or more Fc domains. In some embodiments, the Fc-containing fusion protein comprises one or more Fc domains, each comprising a C-terminal lysine.

In some embodiments, the Fc domain of the Fc-containing fusion protein prolongs a plasma half-life of the Fc-containing fusion protein. In some embodiments, the Fc domain of the Fc-containing fusion protein prolongs the biological activity of the Fc-containing fusion protein. In some embodiments, the Fc domain of the Fc-containing fusion protein decreases the rate of renal clearance of the Fc-containing fusion protein. In some embodiments, the Fc domain of the Fc-containing fusion protein increases the solubility of the Fc-containing fusion protein. In some embodiments, the Fc domain of the Fc-containing fusion protein increases the stability of the Fc-containing fusion protein.

Fc-containing fusion proteins are well known in the art. See, e.g., Czajkowsky et al., *EMBO Mol Med,* 4, 2012. In some embodiments, the Fc-containing fusion protein is an immunoadhesin. In some embodiments, the Fc-containing fusion protein is a cytokine-Fc fusion protein.

In some embodiments, the Fc-containing protein is conjugated to an agent. In some embodiments, the Fc-containing protein is conjugated to at least about 2, 3, 4, 5, 6, 7, 8, 9, or 10 molecules of an agent. In some embodiments, the Fc-containing protein is conjugated to about 2-10, about 4-10, about 6-10, or about 8-10 molecules of an agent. In some embodiments, the Fc-containing protein is conjugated to an agent, wherein the agent is conjugated to the Fc domain of the Fc-containing protein. In some embodiments, the agent is a therapeutic agent. In some embodiments, the therapeutic agent is a small molecule therapeutic agent. In some embodiments, the therapeutic agent is a chemotherapeutic agent. In some embodiments, the agent is a detection agent. In some embodiments, the detection agent is a radiolabel. In some embodiments, the detection agent is a fluorescent label. In some embodiments, the detection agent is an immunolabel. In some embodiments, the Fc-containing protein is a companion diagnostic.

In some embodiments, the Fc-containing protein comprises an IgG1 Fc domain. In some embodiments, the Fc-containing protein comprises an IgG1 Fc domain comprising a C-terminal lysine. In some embodiments, the Fc-containing protein comprises one or more IgG1 Fc domains. In some embodiments, the Fc-containing protein comprises one or more IgG1 Fc domains, each Fc domain comprising a C-terminal lysine. In some embodiments, the Fc-containing protein comprises an IgG1 heavy chain. In some embodiments, the Fc-containing protein comprises an IgG1 heavy chain comprising a C-terminal lysine. In some embodiments, the Fc-containing protein comprises one or more IgG1 heavy chains. In some embodiments, the Fc-containing protein comprises one or more IgG1 heavy chains, each heavy chain comprising a C-terminal lysine.

In some embodiments, the Fc-containing protein comprises an IgG2 Fc domain. In some embodiments, the Fc-containing protein comprises an IgG2 Fc domain comprising a C-terminal lysine. In some embodiments, the Fc-containing protein comprises one or more IgG2 Fc domains. In some embodiments, the Fc-containing protein comprises one or more IgG2 Fc domains, each Fc domain comprising a C-terminal lysine. In some embodiments, the Fc-containing protein comprises an IgG2 heavy chain. In some embodiments, the Fc-containing protein comprises an IgG2 heavy chain comprising a C-terminal lysine. In some embodiments, the Fc-containing protein comprises one or more IgG2 heavy chains. In some embodiments, the Fc-containing protein comprises one or more IgG2 heavy chains, each heavy chain comprising a C-terminal lysine.

In some embodiments, the Fc-containing protein comprises an IgG4 Fc domain. In some embodiments, the Fc-containing protein comprises an IgG4 Fc domain comprising a C-terminal lysine. In some embodiments, the Fc-containing protein comprises one or more IgG4 Fc domains. In some embodiments, the Fc-containing protein comprises one or more IgG4 Fc domains, each Fc domain comprising a C-terminal lysine. In some embodiments, the Fc-containing protein comprises an IgG4 heavy chain. In some embodiments, the Fc-containing protein comprises an IgG4 heavy chain comprising a C-terminal lysine. In some embodiments, the Fc-containing protein comprises one or more IgG4 heavy chains. In some embodiments, the Fc-containing protein comprises one or more IgG4 heavy chains, each heavy chain comprising a C-terminal lysine.

In some embodiments, the Fc-containing protein comprises a post-translational modification. In some embodiments, the post-translational modification is non-enzymatically produced. In some embodiments, the post-translational modification is enzymatically produced. In some embodiments, the post-translational modification is selected from the group consisting of a disulfide pairing, a deamidation, an oxidation, a N-terminal glutamine cyclization, and a glycosylation.

Compositions Comprising a Plurality Fc-Containing Proteins

The present application, in another aspect, provides compositions comprising a plurality of Fc-containing proteins, wherein substantially all Fc-containing proteins of the plurality of Fc-containing proteins has a C-terminal lysine on each Fc domain.

As used herein, the term "substantially all" refers to at least about 90%, including for example, 95%, or 100%. Thus, for example, the composition comprises a plurality of Fc-containing proteins, wherein at least about 90%, 91%, 92%, 93%, 94%, 95%, 96%, 97%, 98%, 99%, or 100% of the Fc-containing proteins of the plurality of Fc-containing proteins have a C-terminal lysine on each Fc domain. In some embodiments, the composition comprises a plurality of Fc-containing proteins, wherein 100% of the Fc-containing proteins of the plurality of Fc-containing proteins have a C-terminal lysine on each Fc domain.

In some embodiments, the composition comprises a plurality of Fc-containing proteins, wherein about 90% to 100% of the Fc-containing proteins of the plurality of Fc-containing proteins have a C-terminal lysine on each Fc domain.

In some embodiments, the composition comprises a plurality of Fc-containing proteins, wherein 100% of the Fc-containing proteins of the plurality of Fc-containing proteins has a C-terminal lysine on each Fc domain.

In some embodiments, the composition comprises a plurality of Fc-containing proteins, wherein substantially all of the Fc-containing proteins of the plurality of Fc-containing proteins have the same amino acid sequence. In some embodiments, the composition comprises a plurality of Fc-containing proteins, wherein substantially all of the Fc-containing proteins of the plurality of Fc-containing proteins have the same Fc domain amino acid sequence. In some embodiments, the composition comprises a plurality of Fc-containing proteins, wherein substantially all of the Fc-containing proteins of the plurality of Fc-containing proteins have the same heavy chain amino acid sequence.

In some embodiments, the composition comprises a plurality of Fc-containing proteins, wherein at least about 80%, 85%, 90%, 95%, or 100% of the Fc-containing proteins of the plurality of Fc-containing proteins have the same amino acid sequence. In some embodiments, the composition comprises a plurality of Fc-containing proteins, wherein at least about 80%, 85%, 90%, 95%, or 100% of the Fc-containing proteins of the plurality of Fc-containing proteins have the same Fc domain amino acid sequence. In some embodiments, the composition comprises a plurality of Fc-containing proteins, wherein at least about 80%, 85%, 90%, 95%, or 100% of the Fc-containing proteins of the plurality of Fc-containing proteins have the same heavy chain amino acid sequence.

In some embodiments, the composition comprises a plurality of Fc-containing proteins, wherein at least about 90% to 100% of the Fc-containing proteins of the plurality of Fc-containing proteins have the same amino acid sequence. In some embodiments, the composition comprises a plurality of Fc-containing proteins, wherein at least about 90% to 100% of the Fc-containing proteins of the plurality of Fc-containing proteins have the same Fc domain amino acid sequence. In some embodiments, the composition comprises a plurality of Fc-containing proteins, wherein at least about 90% to 100% of the Fc-containing proteins of the plurality of Fc-containing proteins have the same heavy chain amino acid sequence.

In some embodiments, the composition comprises a plurality of Fc-containing proteins, wherein 100% of the Fc-containing proteins of the plurality of Fc-containing proteins have the same amino acid sequence. In some embodiments, the composition comprises a plurality of Fc-containing proteins, wherein 100% of the Fc-containing proteins of the plurality of Fc-containing proteins have the same Fc domain amino acid sequence. In some embodiments, the composition comprises a plurality of Fc-containing proteins, wherein 100% of the Fc-containing proteins of the plurality of Fc-containing proteins have the same heavy chain amino acid sequence.

In some embodiments, the composition comprises a plurality of Fc-containing proteins, wherein the plurality of Fc-containing proteins is substantially homogeneous in charge state. As used herein, "substantially homogeneous in charge state" refers to at least about 80%, 85%, 90%, 95%, or 100% of the plurality of Fc-containing proteins having the same charge. It is well appreciated in the art that the charge (e.g., surface charge and net charge) of a Fc-containing protein is highly dependent on the molecular composition of said Fc-containing protein. In some embodiments, the composition comprises a plurality of Fc-containing proteins that is substantially homogeneous in charge state, wherein at least about 80%, 85%, 90%, 95%, or 100% of the plurality of Fc-containing proteins have the same surface charge. In some embodiments, the composition comprises a plurality of Fc-containing proteins that is substantially homogeneous in charge state, wherein at least about 80%, 85%, 90%, 95%, or 100% of the plurality of Fc-containing proteins have the same net charge. In some embodiments, the composition comprises a plurality of Fc-containing proteins that is substantially homogeneous in charge state, wherein each Fc-containing protein of the plurality of Fc-containing proteins has the same charge on an amino acid residue in a position of an amino acid sequence, as compared across each of the plurality of Fc-containing proteins, (e.g., −1, 0, +1). In some embodiments, the composition comprises a plurality of Fc-containing proteins that is substantially homogeneous in charge state, wherein each Fc-containing protein of the plurality of Fc-containing proteins has the same surface charge. In some embodiments, the composition comprises a plurality of Fc-containing proteins that is substantially homogeneous in charge state, wherein each Fc-containing protein of the plurality of Fc-containing proteins has the same net charge. In some embodiments, the composition comprises a plurality of Fc-containing proteins that is substantially homogeneous in charge state, wherein at least about 80%, 85%, 90%, 95%, or 100% of the plurality of Fc-containing proteins have the same pI. In some embodiments, the charge is associated with a Fc-containing protein (e.g., an amino acid residue). In some embodiments, the charge is associated with a post-translational modification of a Fc-containing protein.

In some embodiments, the composition is a pharmaceutical composition. In some embodiments, the pharmaceutical composition is in a form for storage. In some embodiments, the pharmaceutical composition is in a form for product transportation. In some embodiments, the pharmaceutical composition is frozen. In some embodiments, the pharmaceutical composition is lyophilized. In some embodiments, the pharmaceutical composition is reconstituted. In some embodiments, the pharmaceutical composition is an administration composition. In some embodiments, the pharmaceutical composition is in a form for administration to an individual in need thereof.

In some embodiments, the pharmaceutical composition is a sterile pharmaceutical composition. Sterile pharmaceutical formulations are compounded or manufactured according to pharmaceutical-grade sterilization standards (e.g., United States Pharmacopeia Chapters 797, 1072, and 1211; California Business & Professions Code 4127.7; 16 California Code of Regulations 1751, 21 Code of Federal Regulations 21, or ex-U.S. counterparts to such regulations) known to those of skill in the art.

In some embodiments, the pharmaceutical composition is a stable formulation. As used herein, "stable" formulation is one in which the Fc-containing proteins therein essentially retain physical and chemical stability and integrity upon storage. Various analytical techniques for measuring protein stability are available in the art and are reviewed in, for example, Jones, *Adv Drug Delivery Rev,* 10, 1993. Stability can be assessed at a selected temperature for a selected time period. For example, the extent of aggregation during storage can be used as an indicator of protein stability. Thus, a "stable" formulation may be one wherein less than about 10% and preferably less than about 5% of the Fc-containing protein are present as an aggregate in the formulation.

In some embodiments, the pharmaceutical composition is a reconstituted formulation. As used herein, a "reconstituted" formulation is one which has been prepared by dissolving a lyophilized Fc-containing protein formulation in a diluent such that the Fc-containing protein is dispersed throughout. The reconstituted formulation is suitable for administration (e.g. intravenous or subcutaneous administration) to an individual in need there.

In some embodiments, the pharmaceutical composition is an isotonic formulation. As used herein, an "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood.

In some embodiments, the pharmaceutical composition is at a specified pH. In some embodiments, the pharmaceutical composition is at a pH of about 5-7, about 5-6, or about 5-5.5. In some embodiments, the pharmaceutical composition is at a pH of about 5.3. In some embodiments, the pharmaceutical composition is at a pH of about 5.4. In some embodiments, the pharmaceutical composition is pH adjusted.

In some embodiments, the pharmaceutical composition further comprises a pharmaceutically acceptable carrier. As used herein, a "pharmaceutically acceptable carrier" refers to an ingredient in a pharmaceutical composition, other than an active ingredient. A pharmaceutically acceptable carrier includes, but is not limited to, a buffer, excipient, stabilizer, or preservative. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In some embodiments, the pharmaceutically acceptable carrier is selected from the group consisting of sodium acetate, sucrose, polysorbate (e.g., polysorbate 20), sodium succinate, histidine HCl, and sodium chloride.

In some embodiments, the pharmaceutical composition further comprises a pharmaceutically acceptable acid. As used herein, a "pharmaceutically acceptable acid" includes inorganic and organic acids which are non-toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2,2,2]-oct-2-ene-1-carboxylic, glucoheptonic, 4,4'-methylenebis-3-(hydroxy-2-ene-1-carboxylic acid), hydroxynapthoic.

In some embodiments, the pharmaceutical composition further comprises a pharmaceutically acceptable base. As used herein, a "pharmaceutically acceptable base" includes inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

In some embodiments, the pharmaceutical composition further comprises a pharmaceutically acceptable buffer or salt, for example, those derived from both acid and base addition salts of the above indicated acids and bases. Specific buffers and/or salts include histidine, succinate and acetate.

In some embodiments, the pharmaceutical composition further comprises a pharmaceutically acceptable sugar. As used herein, a "pharmaceutically acceptable sugar" is a molecule which, when combined with a Fc-containing protein, significantly prevents or reduces chemical and/or physical instability of the Fc-containing protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, isomaltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

In some embodiments, the pharmaceutical composition further comprises a pharmaceutically acceptable preservative. As used herein, a "pharmaceutically acceptable preservative" is a compound which can be added to the formulations herein to reduce bacterial activity. Examples of potential preservatives include, but are not limited to, octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In some embodiments, the composition comprising a plurality of Fc-containing proteins is a cell culture medium, wherein substantially all Fc-containing proteins have a C-terminal lysine on each Fc domain. In some embodiments, the cell culture medium is a nutrient media. Nutrient media contains all elements needed for host cell growth. In some embodiments, the cell culture medium is a minimal medium. Minimal media contains the minimum nutrients possible for host cell growth, for example, generally without the presence of amino acids. In some embodiments, the cell culture medium is a selective medium. Selective media comprises an agent that inhibits growth of a select organism.

In some embodiments, the cell culture medium further comprises a cell culture medium nutrient for cell support and/or growth. In some embodiments, the cell culture medium nutrient is selected from, for example: proteins; peptides; amino acids; carbohydrates; metals and minerals, for example calcium, magnesium, iron; trace metals, for example, phosphates and sulphates; buffers; pH indicators, for example, phenol red, bromo-cresol purple; and antimicrobial agents.

In some embodiments, the cell culture medium further comprises a host cell. In some embodiment, the culture medium is substantially devoid of a host cell.

In some embodiments, the composition is a cell lysate. In some embodiments, the cell lysate comprises a plurality of Fc-containing proteins and host cell components. In some embodiments, the cell lysate is a centrifuged cell lysate. In some embodiments, the cell lysate comprises a precipitated portion of the cell lysate and a supernatant portion of the cell lysate. In some embodiments, the cell lysate comprises a pelleted portion of the cell lysate and a supernatant portion of the cell lysate.

In some embodiments, the composition is an eluate from a protein purification column. As used herein, "eluate" refers to any fluid that passes through a protein purification column. In some embodiments, the eluate comprises a fluid that is isolated from a flow-through fluid. In some embodiments, the eluate comprises a fluid that is isolated from a wash fluid. In some embodiments, the eluate comprises a fluid that is isolated from one or more wash fluids. In some embodiments, the eluate comprises a fluid that is isolated from an elution fluid.

Protein purification columns for enriching Fc-containing proteins are known in the art. The following are exemplary types of protein purification columns: immunoaffinity, protein A, protein G, ion-exchange, reverse phase, cation-exchange, strong cation-exchange, anion exchange, hydrophobic, mixed modal, hydroxylapatite, and gel filtration.

In some embodiments, the composition is a library of Fc-containing proteins, wherein at least two of the Fc-containing proteins of the plurality of Fc-containing proteins are different. In some embodiments, the library comprises at least two Fc-containing proteins that bind to different antigens. In some embodiments, the library comprises at least two Fc-containing proteins that bind to different epitopes. In some embodiments, the different Fc-containing proteins are contained in different vessels.

In some embodiments, the present invention provides libraries comprising at least 2, 3, 4, 5, 10, 30, 100, 250, 500, 750, 1000, 2500, 5000, 7500, 10000, 25000, 50000, 75000, 100000, 250000, 500000, 750000, 1000000, 2500000, 5000000, 7500000, 10000000, or more than 10000000 different Fc-containing proteins.

Batch

The present application provides large-scale batches (e.g., commercial batches or batches at manufacture scale) of any of the compositions described in the embodiments herein.

In some embodiments, the batch comprises at least about 5 g, 10 g, 50 g, 100 g, 200 g, 300 g, 400 g, 500 g, 600 g, 700 g, 800 g, 900 g, 1,000 g, 1,500 g, 2,000 g, 2,500 g, 3,000 g, 3,500 g, 4,000 g, 4,500 g, or 5,000 g of a plurality of Fc-containing proteins, wherein each Fc-containing protein of the plurality of Fc-containing proteins has a C-terminal lysine on each Fc domain. In some embodiments, the batch comprises at least about 5-5,000 g, 50-4,000 g, or about 100-1,000 g of a plurality of Fc-containing proteins, wherein each Fc-containing protein of the plurality of Fc-containing proteins has a C-terminal lysine on each Fc domain.

In some embodiments, the batch is in a form for drug storage. In some embodiments, the batch is in a form for product transportation. In some embodiments, the batch is in a form for administration to an individual in need thereof. In some embodiments, the batch is lyophilized. In some embodiments, the batch is not conjugated to an agent. In some embodiments, the batch is conjugated to an agent. In some embodiments, the batch further comprises a formulation component.

In some embodiments, the batch is a cell culture medium. In some embodiments the batch is a cell lysate.

In some embodiments, the batch, or a portion thereof, is in a vessel. In some embodiments, the batch, or portion thereof, is in a vial. In some embodiments, the batch, or portion thereof, is in a plurality of vials. In some embodiments, the batch, or portion thereof, is in a syringe.

In some embodiments, the batch, or a portion thereof, is in a plurality of vials, wherein each vial comprises a plurality of Fc-containing proteins, wherein each Fc-containing protein has a C-terminal lysine on each Fc domain. In some embodiments, the batch, or a portion thereof, is in a plurality of vials, wherein each vial comprises a plurality of Fc-containing proteins, wherein at least about 90%, 91%, 92%, 93%, 94%, 95%, 96%, 97%, 98%, 99%, or 100% of the plurality of Fc-containing protein in each vial has a C-terminal lysine on each Fc domain. In some embodiments, the batch, or a portion thereof, is in a plurality of vials, wherein at least about 50%, 55%, 60%, 65%, 70%, 75%, 80%, 85%, 90%, 95%, or 100% of the vials comprise at least about 90%, 91%, 92%, 93%, 94%, 95%, 96%, 97%, 98%, 99%, or 100% of the plurality of Fc-containing proteins comprising a C-terminal lysine on each Fc domain.

In some embodiments, the batch is aliquoted into a unit dosage. As used herein, a "unit dosage" is the amount of Fc-containing protein intended for administration as a single unit dose. In some embodiments, the single unit dose is about 1 to about 500 mg of a Fc-containing protein. In some embodiments, the unit dosage is packaged in a container. In some embodiments, the unit dosage is packaged in a vial.

In some embodiments, the size of the commercial batch is no greater than about 1, 2, 3, 4, 5, 6, 7, 8, 9, or 10 times the size of the clinical batch. As used herein, "commercial batch" refers to an amount of Fc-containing protein produced during one or more production runs completed for purposes of commercial production and/or distribution. As used herein, "clinical batch" refers to an amount of Fc-containing protein produced during one or more production runs completed for purposes of clinical testing. In some embodiments, the size of the commercial batch is no greater than 10 times the size of the clinical batch.

In some embodiments, the vessel comprises an aliquot of a commercial batch as described herein, wherein the commercial batch comprises a composition comprising a Fc-containing protein, wherein each Fc domain of the Fc-containing protein has a C-terminal lysine. In some embodiments, the vial comprises an aliquot of a commercial batch as described herein, wherein the commercial batch comprises a composition comprising a Fc-containing protein, wherein each Fc domain of the Fc-containing protein has a C-terminal lysine. In some embodiments, the syringe comprises an aliquot of a commercial batch as described herein, wherein the commercial batch comprises a composition comprising a Fc-containing protein, wherein each Fc domain of the Fc-containing protein has a C-terminal lysine.

Cell Culture System

The invention provides a cell culture system comprising any host cell described in the embodiments herein.

In some embodiments, the cell culture system maintains a host cell in an environment for the production of a Fc-containing protein. In some embodiments, the cell culture system maintains a host cell in an environment for growth.

In some embodiments, the cell culture system comprises a seed culture. In some embodiments, the cell culture system comprises an inoculum culture. In some embodiments, the inoculum culture is a primary inoculum culture. In some embodiments, the inoculum culture is a secondary inoculum. In some embodiments, the cell culture system comprises a production culture.

In some embodiments, the cell culture system comprises a mechanism for maintaining a host cell in a specified environment. In some embodiments, the specified environment is a specified temperature. In some embodiments, the specified temperature is about 15° C. to about 45° C. In some embodiments, the specified temperature is about 30° C. In some embodiments, the specified environment is a specified pH. In some embodiments, the specified environment is a specified dissolved oxygen concentration. In some embodiments, the specified environment is a specified nutrient level.

In some embodiments, the cell culture further comprises a culture medium. In some embodiments, the cell culture system comprises a seed culture. In some embodiments, the culture medium is an inoculum culture. In some embodiments, the inoculum culture medium is a primary inoculum culture medium. In some embodiments, the inoculum culture medium is a secondary inoculum medium. In some embodiments, the culture medium is a production culture medium.

In some embodiments, the culture system comprises a Fc-containing protein as described in the embodiments herein. In some embodiments, the culture system comprises a plurality of Fc-containing protein as described in the embodiments herein. In some embodiments, the culture system comprises a composition comprising a Fc-containing protein as described in the embodiments herein.

In some embodiments, the culture system comprises a Fc-containing protein, wherein each Fc domain of the Fc-containing protein has a C-terminal lysine. In some embodiments, the culture system comprises a plurality of Fc-containing protein, wherein each Fc-containing protein of the plurality of Fc-containing proteins has a C-terminal lysine Fc domain. In some embodiments, the culture system comprises a composition comprising a plurality of Fc-containing protein, wherein each Fc-containing protein of the plurality of Fc-containing proteins has a C-terminal lysine on each Fc domain.

Methods of Producing a Host Cell with a Reduction of a CpD Expression Level

The present application provides methods of producing any host cell described in the embodiments herein, wherein the methods comprise inactivating the CpD gene of the host cell.

Generally, the methods of producing a host cell comprise inactivating the CpD gene of the host cell. In some embodiments, the method of producing a host cell, wherein the host cell has a reduction of a CpD expression level, comprises inactivating the CpD gene using a siRNA system. In some embodiments, the method of producing a host cell comprises inactivating the CpD gene using a siRNA system comprising a siRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the method of producing a host cell comprises inactivating the CpD gene using a siRNA system comprising a siRNA nucleotide sequence that is approximately 10-25 nucleotides in length. In some embodiments, the method of producing a host cell comprises inactivating the CpD gene using a siRNA system comprising a siRNA nucleotide sequence that is approximately 15-25 nucleotides in length. In some embodiments, the method of producing a host cell comprises inactivating the CpD gene using a siRNA system comprising a siRNA nucleotide sequence that is at least about 10, at least about 15, at least about 20, or at least about 25 nucleotides in length. In some embodiments, the method of producing a host cell comprises inactivating the CpD gene using a siRNA system comprising a nucleotide sequence that is at least about 80%, at least about 85%, at least about 90%, at least about 95%, or 100% complementary to a region of a CpD mRNA molecule. In some embodiments, the method of producing a host cell comprises inactivating the CpD gene using a siRNA system comprising a siRNA nucleotide sequence that is at least at least about 80%, at least about 85%, at least about 90%, at least about 95%, or 100% complementary to a region of a CpD pro-mRNA molecule. In some embodiments, the method of producing a host cell comprises inactivating the CpD gene using a siRNA system comprising a double stranded RNA molecule. In some embodiments, the method of producing a host cell comprises inactivating the CpD gene using a siRNA system comprising a single stranded RNA molecule. Exemplary CpD siRNA nucleotide sequences are listed in Table 1.

In some embodiments, the method of producing a host cell comprises delivering a siRNA system to a host cell. In some embodiments, the method of producing a host cell comprises delivering a siRNA system to a host cell, wherein the siRNA system comprises a siRNA nucleotide sequence. In some embodiments, the method of producing a host cell comprises delivering a siRNA system to the host cell using electroporation. In some embodiments, the method of producing a host cell comprises delivering a siRNA system to the host cell using transfection techniques. In some embodiments, the method of producing a host cell comprises delivering a siRNA system to the host cell using a virus.

In some embodiments, the method of producing a host cell, wherein the host cell has a reduced level of CpD expression, further comprises determining the level of CpD gene inactivation in the host cell. In some embodiments, determining the level of CpD gene inactivation comprises determining a level of CpD expression prior to delivering a siRNA nucleotide sequence to the host cell. In some embodiments, determining the level of CpD gene inactivation comprises determining a level of CpD expression after delivering a siRNA nucleotide sequence to the host cell. In some embodiments, the level of CpD expression is determined at the RNA level. In some embodiments, the method of determining the level of CpD gene inactivation comprises determining the level of CpD expression using PCR. In some embodiments, the level of CpD expression is determined at the protein level. In some embodiments, the method of determining the level of CpD gene inactivation comprises determining the CpD expression level using immunohistochemistry. In some embodiments, the method of determining the level of CpD gene inactivation comprises determining the CpD expression level using Western blot. In some embodiments, the method of determining the level of CpD gene inactivation comprises determining the CpD expression level using flow cytometry. In some embodiments, the level of CpD gene inactivation is determined by comparing the level of CpD expression after delivery of a siRNA to a control value. In some embodiments, the level of CpD gene inactivation is determined by comparing the level of CpD expression after delivery of a siRNA to a wild type value. In some embodiments, the level of CpD gene inactivation is determined by comparing a level of CpD expression after delivery of a siRNA to a level of CpD expression prior to delivery of a CpD siRNA.

Exemplary primers and probes for determining the level of CpD at the RNA level are provided in Table 2.

TABLE 2

Exemplary nucleotide sequences for determining the RNA expression level of CpD.

| | SEQ ID NO.: | Nucleotide sequence: |
|---|---|---|
| CpD forward primer | 1 | CCC ACA CAT TAC AAA TCT TAC CA |
| CpD reverse primer | 2 | GAG ATT TCG AGG GAC CAA AT |
| CpD probe | 3 | TTG GGA CAG AGT GCT GAG TAT CGT CA |

In some embodiments, the method of producing a host cell, wherein the host cell has a reduced level of CpD expression, comprises inactivating the CpD gene using a shRNA system. In some embodiments, the method of producing a host cell comprises inactivating the CpD gene using a shRNA system comprising a shRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the method of producing a host cell comprises inactivating the CpD gene using a shRNA system comprising a shRNA nucleotide sequence that is approximately 10-25 nucleotides in length. In some embodiments, the method of producing a host cell comprises inactivating the CpD gene using a shRNA system comprising a shRNA nucleotide sequence that is approximately 15-25 nucleotides in length. In some embodiments, the method of producing a host cell comprises inactivating the CpD gene using a shRNA system comprising a shRNA nucleotide sequence that is at least about 10, at least about 15, at least about 20, or at least about 25 nucleotides in length. In some embodiments, the method of producing a host cell comprises inactivating the CpD gene using a shRNA system comprising a nucleotide sequence that is at least about 80%, at least about 85%, at least about 90%, at least about 95%, or 100% complementary to a region of a CpD mRNA molecule. In some embodiments, the method of producing a host cell comprises inactivating the CpD gene using a shRNA system comprising a shRNA nucleotide sequence that is at least at least about 80%, at least about 85%, at least about 90%, at least about 95%, or 100% complementary to a region of a CpD pro-mRNA molecule. In some embodiments, the method of producing a host cell comprises inactivating the CpD gene using a shRNA system comprising a double stranded RNA molecule. In some embodiments, the method of producing a host cell comprises inactivating the CpD gene using a shRNA system comprising a single stranded RNA molecule. Exemplary CpD shRNA nucleotide sequences are listed in Table 1.

In some embodiments, the method of producing a host cell comprises delivering a shRNA system to a host cell. In some embodiments, the method of producing a host cell comprises delivering a shRNA system to a host cell, wherein the shRNA system comprises a shRNA nucleotide sequence. In some embodiments, the method of producing a host cell comprises delivering a shRNA system to the host cell using electroporation. In some embodiments, the method of producing a host cell comprises delivering a shRNA system to the host cell using transfection techniques. In some embodiments, the method of producing a host cell comprises delivering a shRNA system to the host cell using a virus.

In some embodiments, the method of producing a host cell, wherein the host cell has a reduced level of CpD expression, further comprises determining the level of CpD gene inactivation in the host cell. In some embodiments, determining the level of CpD gene inactivation comprises determining a level of CpD expression prior to delivering a shRNA nucleotide sequence to the host cell. In some embodiments, determining the level of CpD gene inactivation comprises determining a level of CpD expression after delivering a shRNA nucleotide sequence to the host cell. In some embodiments, the level of CpD expression is determined at the RNA level. In some embodiments, the method of determining the level of CpD gene inactivation comprises determining the level of CpD expression using PCR. In some embodiments, the level of CpD expression is determined at the protein level. In some embodiments, the method of determining the level of CpD gene inactivation comprises determining the CpD expression level using immunohistochemistry. In some embodiments, the method of determining the level of CpD gene inactivation comprises determining the CpD expression level using Western blot. In some embodiments, the method of determining the level of CpD gene inactivation comprises determining the CpD expression level using flow cytometry. In some embodiments, the level of CpD gene inactivation is determined by comparing the level of CpD expression after delivery of a shRNA to a control value. In some embodiments, the level of CpD gene inactivation is determined by comparing the level of CpD expression after delivery of a shRNA to a wild type value. In some embodiments, the level of CpD gene inactivation is determined by comparing a level of CpD expression after delivery of a shRNA to a level of CpD expression prior to delivery of a CpD shRNA.

Exemplary primers and probes for determining the level of CpD at the RNA level are provided in Table 2.

Additionally provided in the present application are methods of producing a host cell by gene deletion or gene addition or substitution. For example, methods include, but are not limited to use of CRISPR, TALEN, ZFN, and meganuclease systems.

Generally, a CRISPR system comprises a caspase protein, such as Cas9, and an RNA sequence comprising a nucleotide sequence, referred to as a guide sequence, that is complementary to a sequence of interest. The caspase and RNA sequence form a complex that identify a DNA sequence of a host cell, and subsequently the nuclease activity of the caspase allows for cleavage of the DNA strand. Caspases isotypes have single-stranded DNA or double-stranded DNA nuclease activity. Design of guide RNA sequences and number of guide RNA sequences used in a CRISPR system allow for removal of a specific stretch of a gene and/or addition of a DNA sequence.

In some embodiments, the method of producing a host cell, wherein the host cell has a reduced level of CpD expression, comprises inactivating the CpD gene using a CRISPR system. In some embodiments, the method of producing a host cell comprises inactivating the CpD gene using a CRISPR system comprising a coding vector. In some embodiments, the method of producing a host cell comprises inactivating the CpD gene using a CRISPR system comprising a coding vector comprising a DNA endonuclease gene. In some embodiments, the method of producing a host cell comprises inactivating the CpD gene using a CRISPR system comprising a coding vector comprising a CAS gene. In some embodiments, the method of producing a host cell comprises inactivating the CpD gene using a CRISPR system comprising a coding vector comprising a CAS9 gene. In some embodiments, the method of producing a host cell comprises inactivating the CpD gene using a CRISPR system comprising a coding vector encoding a CAS9 gene. In some embodiments, the method of producing a host cell comprises inactivating the CpD gene using a CRISPR system comprising a Cas protein. In some embodiments, the method of producing a host cell comprises inactivating the CpD gene using a CRISPR system comprising a Cas9 protein. In some embodiments, the method of producing a host cell comprises inactivating the CpD gene using a CRISPR system comprising a coding vector encoding a RNA molecule capable of interacting with the Cas9 protein. In some embodiments, the method of producing a host cell comprises inactivating the CpD gene using a CRISPR system comprising a coding vector encoding a RNA molecule comprising a guide RNA (gRNA) unit, wherein the gRNA unit comprises a nucleotide sequence that is complementary to a portion of a CpD gene sequence. In some embodiments, the method of producing a host cell comprises inactivating the CpD gene using a CRISPR system comprising a RNA molecule comprising a gRNA unit, wherein the gRNA unit comprises a nucleotide sequence that is complementary to a portion of a CpD gene sequence. In some embodiments, the method of producing a host cell comprises inactivating the CpD gene using a CRISPR system comprising a coding vector encoding a RNA molecule comprising a trans-activating crRNA (tracrRNA) unit. In some embodiments, the method of producing a host cell comprises inactivating the CpD gene using a CRISPR system comprising a RNA molecule comprising a tracrRNA unit. In some embodiments, the method of producing a host cell comprises inactivating the CpD gene using a CRISPR system comprising a coding vector encoding a RNA molecule comprising a gRNA unit and a tracrRNA unit, wherein the gRNA unit comprises a nucleotide sequence that is complementary to a portion of a gene sequence. In some embodiments, the method of producing a host cell comprises inactivating the CpD gene using a CRISPR system comprising a RNA molecule comprising a gRNA unit and a tracrRNA unit, wherein the gRNA unit comprises a nucleotide sequence that is complementary to a portion of a CpD gene sequence. In some embodiments, the method of producing a host cell comprises inactivating the CpD gene using a CRISPR system comprising: a) a first RNA molecule comprising a gRNA unit, wherein the gRNA unit comprises a first nucleotide sequence that is complementary to a portion of a CpD gene sequence; and b) a second RNA molecule comprising a gRNA unit, wherein the gRNA unit comprises a second nucleotide sequence that is complementary to a portion of a CpD gene sequence. In some embodiments, the first nucleotide sequence and second nucleotide sequence are different. In some embodiments, the first nucleotide sequence is complementary to a portion of a CpD gene sequence that is in a different location than the region of the portion of the CpD gene that is complementary to the second nucleotide sequence.

Exemplary CpD target sequences included in gRNA sequences are listed in Table 3.

TABLE 3

Exemplary CpD target sequences included in gRNA.

| SEQ ID NO.: | CpD target sequence: |
|---|---|
| 21 | GAA GAC GAG ACT TTC AAA GAC GG |
| 22 | TCA GTT AGG TGG CTT AGG TTC GG |

In some embodiments, the method of producing a host cell comprises delivering a CRISPR system to the host cell. In some embodiments, the method of producing a host cell comprises delivering a vector comprising a CRISPR system using a delivery vector. In some embodiments, the delivery vector is a virus vector. In some embodiments, the delivery vector is a lentivirus. In some embodiments, the delivery vector is an adenovirus. In some embodiments, the vector comprises a promoter.

Generally, a TALEN system comprises one or more restriction nucleases and two or more protein complexes that allow for recognition of a DNA sequence and subsequent double-stranded DNA cleavage. A protein complex of the TALEN system comprises a number of transcription activator-like effectors (TALEs), each recognizing a specific nucleotide, and a domain of a restriction nuclease. Generally, a TALEN system is designed so that two protein complexes, each comprising TALEs and a domain of a restriction nuclease, will individually bind to DNA sequences in a manner to allow for the two domains (one from each protein complex) of a restriction nuclease to form an active nuclease and cleave a specific DNA sequence. Design of number of protein complexes and sequences to be cleaved in a TALEN system allows for removal of a specific stretch of a gene and/or addition of a DNA sequence.

In some embodiments, the method of producing a host cell, wherein the host cell has a reduced level of CpD expression, comprises inactivating the CpD gene using a TALEN system. In some embodiments, the method of producing a host cell comprises inactivating the CpD gene using a TALEN system comprising a first TALEN unit. In some embodiments, the first TALEN unit comprises a first TALEN binding unit. In some embodiments, the first TALEN binding unit comprises at least one transcription activator-like effector (TALE) and a first nuclease domain. In some embodiments, the first TALEN binding unit comprises at least 3, 4, 5, 6, 7, 8, 9, 10, 11, 12, 13, 14, or 15 TALEs and a first nuclease domain, wherein the TALEs are linked together, and wherein the linked TALEs recognize a portion of a CpD nucleotide sequence. In some embodiments, the first TALEN binding unit comprises at least 3, 4, 5, 6, 7, 8, 9, 10, 11, 12, 13, 14, or 15 TALEs and a first nuclease domain, wherein the TALEs are linked together, wherein the linked TALEs recognize a portion of a CpD nucleotide sequence, and wherein the linked TALEs are further linked to the first nuclease domain. In some embodiments, the first TALEN unit further comprises a second TALEN binding unit. In some embodiments, the second TALEN binding unit comprises at least one transcription activator-like effector (TALE) and a second nuclease domain. In some embodiments, the second TALEN binding unit comprises at least 3, 4, 5, 6, 7, 8, 9, 10, 11, 12, 13, 14, or 15 TALEs and a second nuclease domain, wherein the TALEs are linked together, and wherein the linked TALEs recognize a portion of a CpD nucleotide sequence. In some embodiments, the second TALEN binding unit comprises at least 3, 4, 5, 6, 7, 8, 9, 10, 11, 12, 13, 14, or 15 TALEs and a second nuclease domain, wherein the TALEs are linked together, wherein the linked TALEs recognize a portion of a CpD nucleotide sequence, and wherein the linked TALEs are further linked to the second nuclease domain. In some embodiments, the first TALEN binding unit and second TALEN binding unit bind to different sequences of the CpD gene. In some embodiments, the first nuclease domain is a domain of an endonuclease. In some embodiments, the first nuclease domain is a domain of a restriction endonuclease. In some embodiments, the first nuclease domain is a domain of Fok1. In some embodiments, the second nuclease domain is a domain of an endonuclease. In some embodiments, the second nuclease domain is a domain of a restriction endonuclease. In some embodiments, the second nuclease domain is a domain of Fok1. In some embodiments, the first nuclease domain and second nuclease domain associate to comprise an active restriction endonuclease. In some embodiments, the first nuclease domain and second nuclease domain associate to comprise an active Fok1 enzyme.

In some embodiments, the method of producing a host cell comprises inactivating the CpD gene using a TALEN system further comprising a second TALEN unit. In some embodiments, the second TALEN unit comprises a third TALEN binding unit. In some embodiments, the third TALEN binding unit comprises at least one transcription activator-like effector (TALE) and a third nuclease domain. In some embodiments, the third TALEN binding unit comprises at least 3, 4, 5, 6, 7, 8, 9, 10, 11, 12, 13, 14, or 15 TALEs and a third nuclease domain, wherein the TALEs are linked together, and wherein the linked TALEs recognize a portion of a CpD nucleotide sequence. In some embodiments, the third TALEN binding unit comprises at least 3, 4, 5, 6, 7, 8, 9, 10, 11, 12, 13, 14, or 15 TALEs and a third nuclease domain, wherein the TALEs are linked together, wherein the linked TALEs recognize a portion of a CpD nucleotide sequence, and wherein the linked TALEs are further linked to the third nuclease domain. In some embodiments, the second TALEN unit further comprises a fourth TALEN binding unit. In some embodiments, the fourth TALEN binding unit comprises at least one transcription activator-like effector (TALE) and a fourth nuclease domain. In some embodiments, the fourth TALEN binding unit comprises at least 3, 4, 5, 6, 7, 8, 9, 10, 11, 12, 13, 14, or 15 TALEs and a fourth nuclease domain, wherein the TALEs are linked together, and wherein the linked TALEs recognize a portion of a CpD nucleotide sequence. In some embodiments, the fourth TALEN binding unit comprises at least 3, 4, 5, 6, 7, 8, 9, 10, 11, 12, 13, 14, or 15 TALEs and a fourth nuclease domain, wherein the TALEs are linked together, wherein the linked TALEs recognize a portion of a CpD nucleotide sequence, and wherein the linked TALEs are further linked to the fourth nuclease domain. In some embodiments, the third TALEN binding unit and fourth TALEN binding unit bind to different sequences of the CpD gene. In some embodiments, the third nuclease domain is a domain of an endonuclease. In some embodiments, the third nuclease domain is a domain of a restriction endonuclease. In some embodiments, the third nuclease domain is a domain of Fok1. In some embodiments, the fourth nuclease domain is a domain of an endonuclease. In some embodiments, the fourth nuclease domain is a domain of a restriction endonuclease. In some embodiments, the fourth nuclease domain is a domain of Fok1. In some embodiments, the third nuclease domain and fourth nuclease domain associate to comprise an active restriction endonuclease. In some embodiments, the third nuclease domain and fourth nuclease domain associate to comprise an active Fok1 enzyme.

In some embodiments, the method of producing a host cell, wherein the host cell has a reduced level of CpD expression, comprises inactivating the CpD gene using a TALEN system, wherein the TALEN system comprises a first TALEN unit and a second TALEN unit that bind to different, non-overlapping portions of a CpD gene sequence.

In some embodiments, the method of producing a host cell, wherein the host cell has a reduced level of CpD expression, comprises inactivating the CpD gene using a TALEN system, wherein the TALEN system comprises a coding vector encoding a first TALEN unit. In some embodiments, the method of producing a host cell, wherein the host cell has a reduced level of CpD expression, comprises inactivating the CpD gene using a TALEN system, wherein the TALEN system comprises a coding vector encoding a first TALEN unit, wherein the TALEN system comprises a coding vector encoding a second TALEN unit. In some embodiments, the method of producing a host cell, wherein the host cell has a reduced level of CpD expression, comprises inactivating the CpD gene using a TALEN system, wherein the TALEN system comprises a coding vector encoding a first TALEN unit, wherein the TALEN system comprises a coding vector encoding a first TALEN unit and a second TALEN unit.

In some embodiments, the method of producing a host cell, wherein the host cell has a reduced level of CpD expression, comprises inactivating the CpD gene using a TALEN system, wherein the TALEN system comprises a first TALEN unit. In some embodiments, the method of producing a host cell, wherein the host cell has a reduced level of CpD expression, comprises inactivating the CpD gene using a TALEN system, wherein the TALEN system comprises a second TALEN unit. In some embodiments, the method of producing a host cell, wherein the host cell has a reduced level of CpD expression, comprises inactivating the CpD gene using a TALEN system, wherein the TALEN system comprises a first TALEN unit and a second TALEN unit.

In some embodiments, the first TALEN binding unit comprises a group of linked TALEs, wherein the group of TALEs recognize a nucleotide sequence. In some embodiments, the nucleotide sequence is a sequence comprising a portion of a CpD gene. In some embodiments, the nucleotide sequence is a sequence comprising a portion of a CpD gene promoter. In some embodiments, the nucleotide sequence is a sequence comprising a portion of a sequence flanking a CpD gene. In some embodiments, the sequence is at least about 80%, at least about 85%, at least about 90%, at least about 95%, or 100% homologous to a portion of a CpD gene. In some embodiments, the sequence is at least about 80%, at least about 85%, at least about 90%, at least about 95%, or 100% homologous to a portion of a CpD gene promoter. In some embodiments, the sequence is at least about 80%, at least about 85%, at least about 90%, at least about 95%, or 100% homologous to a portion of a sequence flanking a CpD gene.

In some embodiments, the method of producing a host cell comprises delivering a TALEN system to the host cell. In some embodiments, the method of producing a host cell comprises delivering a vector comprising a TALEN system using a delivery vector. In some embodiments, the delivery vector is a virus vector. In some embodiments, the delivery vector is a lentivirus. In some embodiments, the delivery vector is an adenovirus.

Generally, a ZFN system comprises one or more restriction nucleases and two or more protein complexes that allow for recognition of a DNA sequence and subsequent double-stranded DNA cleavage. A protein complex of the ZFN system comprises a number of zinc fingers, each recognizing a specific nucleotide codon, and a domain of a restriction nuclease. Generally, a ZFN system is designed so that two protein complexes, each comprising zinc fingers and a domain of a restriction nuclease, will individually bind to DNA sequences in a manner to allow for the two domains (one from each protein complex) of a restriction nuclease to form an active nuclease and cleave a specific DNA sequence. Design of number of protein complexes and sequences to be cleaved in a ZFN system allows for removal of a specific stretch of a gene and/or addition of a DNA sequence.

In some embodiments, the method of producing a host cell, wherein the host cell has a reduced level of CpD expression, comprises inactivating the CpD gene using a ZFN system. In some embodiments, the method of producing a host cell comprises inactivating the CpD gene using a ZFN system comprising a first ZFN unit. In some embodiments, the first ZFN unit comprises a first ZFN binding unit. In some embodiments, the first ZFN binding unit comprises at least one zinc finger and a first nuclease domain. In some embodiments, the first ZFN binding unit comprises at least 2, 3, 4, 5, 6, 7, 8, 9, or 10 zinc fingers and a first nuclease domain, wherein the zinc fingers are linked together, and wherein the linked zinc fingers recognize a portion of a CpD nucleotide sequence. In some embodiments, the first ZFN binding unit comprises at least 2, 3, 4, 5, 6, 7, 8, 9, or 10 zinc fingers and a first nuclease domain, wherein the zinc fingers are linked together, wherein the linked zinc fingers recognize a portion of a CpD nucleotide sequence, and wherein the linked zinc fingers are further linked to the first nuclease domain. In some embodiments, the first ZFN unit further comprises a second ZFN binding unit. In some embodiments, the second ZFN binding unit comprises at least one zinc finger and a second nuclease domain. In some embodiments, the second ZFN binding unit comprises at least 2, 3, 4, 5, 6, 7, 8, 9, or 10 zinc fingers and a second nuclease domain, wherein the zinc fingers are linked together, and wherein the linked zinc fingers recognize a portion of a CpD nucleotide sequence. In some embodiments, the second ZFN binding unit comprises at least 2, 3, 4, 5, 6, 7, 8, 9, or 10 zinc fingers and a second nuclease domain, wherein the zinc fingers are linked together, wherein the linked zinc fingers recognize a portion of a CpD nucleotide sequence, and wherein the linked zinc fingers are further linked to the second nuclease domain. In some embodiments, the first ZFN binding unit and second ZFN binding unit bind to different sequences of the CpD gene. In some embodiments, the first nuclease domain is a domain of an endonuclease. In some embodiments, the first nuclease domain is a domain of a restriction endonuclease. In some embodiments, the first nuclease domain is a domain of Fok1. In some embodiments, the second nuclease domain is a domain of an endonuclease. In some embodiments, the second nuclease domain is a domain of a restriction endonuclease. In some embodiments, the second nuclease domain is a domain of Fok1. In some embodiments, the first nuclease domain and second nuclease domain associate to comprise an active restriction endonuclease. In some embodiments, the first nuclease domain and second nuclease domain associate to comprise an active Fok1 enzyme.

In some embodiments, the method of producing a host cell comprises inactivating the CpD gene using a ZFN system further comprising a second ZFN unit. In some embodiments, the second ZFN unit comprises a third ZFN binding unit. In some embodiments, the third ZFN binding unit comprises at least one zinc finger and a third nuclease domain. In some embodiments, the third ZFN binding unit comprises at least 2, 3, 4, 5, 6, 7, 8, 9, or 10 zinc fingers and a third nuclease domain, wherein the zinc fingers are linked together, and wherein the linked zinc fingers recognize a portion of a CpD nucleotide sequence. In some embodiments, the third ZFN binding unit comprises at least 2, 3, 4, 5, 6, 7, 8, 9, or 10 zinc fingers and a third nuclease domain, wherein the zinc fingers are linked together, wherein the linked zinc fingers recognize a portion of a CpD nucleotide sequence, and wherein the linked zinc fingers are further linked to the third nuclease domain. In some embodiments, the second ZFN unit further comprises a fourth ZFN binding unit. In some embodiments, the fourth ZFN binding unit comprises at least one zinc finger and a fourth nuclease domain. In some embodiments, the fourth ZFN binding unit comprises at least 2, 3, 4, 5, 6, 7, 8, 9, or 10 zinc fingers and a fourth nuclease domain, wherein the zinc fingers are linked together, and wherein the linked zinc fingers recognize a portion of a CpD nucleotide sequence. In some embodiments, the fourth ZFN binding unit comprises at least 2, 3, 4, 5, 6, 7, 8, 9, or 10 zinc fingers and a fourth nuclease domain, wherein the zinc fingers are linked together, wherein the linked zinc fingers recognize a portion of a CpD nucleotide sequence, and wherein the linked zinger fingers are further linked to the fourth nuclease domain. In some embodiments, the third ZFN binding unit and fourth ZFN binding unit bind to different sequences of the CpD gene. In some embodiments, the third nuclease domain is a domain of an endonuclease. In some embodiments, the third nuclease domain is a domain of a restriction endonuclease. In some embodiments, the third nuclease domain is a domain of Fok1. In some embodiments, the fourth nuclease domain is a domain of an endonuclease. In some embodiments, the fourth nuclease domain is a domain of a restriction endonuclease. In some embodiments, the fourth nuclease domain is a domain of Fok1. In some embodiments, the third nuclease domain and fourth nuclease domain associate to comprise an active restriction endonuclease. In some embodiments, the third nuclease domain and fourth nuclease domain associate to comprise an active Fok1 enzyme.

In some embodiments, the method of producing a host cell, wherein the host cell has a reduced level of CpD expression, comprises inactivating the CpD gene using a ZFN system, wherein the ZFN system comprises a first ZFN unit and a second TALEN unit that bind to different, non-overlapping portions of a CpD gene sequence.

In some embodiments, the method of producing a host cell, wherein the host cell has a reduced level of CpD expression, comprises inactivating the CpD gene using a ZFN system, wherein the ZFN system comprises a coding vector encoding a first ZFN unit. In some embodiments, the method of producing a host cell, wherein the host cell has a reduced level of CpD expression, comprises inactivating the CpD gene using a ZFN system, wherein the ZFN system comprises a coding vector encoding a first ZFN unit, wherein the ZFN system comprises a coding vector encoding a second ZFN unit. In some embodiments, the method of producing a host cell, wherein the host cell has a reduced level of CpD expression, comprises inactivating the CpD gene using a ZFN system, wherein the ZFN system comprises a coding vector encoding a first ZFN unit, wherein the ZFN system comprises a coding vector encoding a first ZFN unit and a second ZFN unit.

In some embodiments, the method of producing a host cell, wherein the host cell has a reduced level of CpD expression, comprises inactivating the CpD gene using a ZFN system, wherein the ZFN system comprises a first ZFN unit. In some embodiments, the method of producing a host cell, wherein the host cell has a reduced level of CpD expression, comprises inactivating the CpD gene using a ZFN system, wherein the ZFN system comprises a second ZFN unit. In some embodiments, the method of producing a host cell, wherein the host cell has a reduced level of CpD expression, comprises inactivating the CpD gene using a ZFN system, wherein the ZFN system comprises a first ZFN unit and a second ZFN unit.

In some embodiments, the first ZFN binding unit comprises a group of linked zinc fingers, wherein the group of zinc fingers recognize a nucleotide sequence. In some embodiments, the nucleotide sequence is a sequence comprising a portion of a CpD gene. In some embodiments, the nucleotide sequence is a sequence comprising a portion of a CpD gene promoter. In some embodiments, the nucleotide sequence is a sequence comprising a portion of a sequence flanking a CpD gene. In some embodiments, the sequence is at least about 80%, at least about 85%, at least about 90%, at least about 95%, or 100% homologous to a portion of a CpD gene. In some embodiments, the sequence is at least about 80%, at least about 85%, at least about 90%, at least about 95%, or 100% homologous to a portion of a CpD gene promoter. In some embodiments, the sequence is at least about 80%, at least about 85%, at least about 90%, at least about 95%, or 100% homologous to a portion of a sequence flanking a CpD gene.

In some embodiments, the method of producing a host cell comprises delivering a ZFN system to the host cell. In some embodiments, the method of producing a host cell comprises delivering a vector comprising a ZFN system using a delivery vector. In some embodiments, the delivery vector is a virus vector. In some embodiments, the delivery vector is a lentivirus. In some embodiments, the delivery vector is an adenovirus.

Generally, a meganuclease system comprises one or more meganucleases that allow for recognition of a DNA sequence and subsequent double-stranded DNA cleavage.

In some embodiments, the method of producing a host cell, wherein the host cell has a reduced level of CpD expression, comprises inactivating the CpD gene using a meganuclease system. In some embodiments, the meganuclease has a DNA recognition sequence that is about 8 to about 35 nucleotide base pairs in length. In some embodiments, the meganuclease has a DNA recognition sequence that is about 12 to about 30 nucleotide base pairs in length. In some embodiments, the DNA recognition sequence is a sequence comprising a portion of a CpD gene. In some embodiments, the DNA recognition sequence is a sequence comprising a portion of a CpD gene promoter. In some embodiments, the DNA recognition sequence is a sequence comprising a portion of a sequence flanking a CpD gene.

In some embodiments, the method of producing a host cell comprises delivering a meganuclease system to the host cell. In some embodiments, the method of producing a host cell comprises delivering a vector comprising a meganuclease system using a delivery vector. In some embodiments, the delivery vector is a virus vector. In some embodiments, the delivery vector is a lentivirus. In some embodiments, the delivery vector is an adenovirus.

In some embodiments, the method of producing a host cell, wherein the host cell has a reduced level of CpD expression, further comprises determining a level of CpD gene inactivation, such as gene deletion or gene addition or substitution. In some embodiments, the method of producing a host cell comprises determining the level of CpD gene inactivation, wherein a CpD gene deletion is detected. In some embodiments, the method of producing a host cell comprises determining the level of CpD gene inactivation, wherein a CpD gene addition or substitution is detected. In some embodiments, the method of producing a host cell comprises determining the level of CpD gene inactivation, wherein a level of CpD expression is determined prior to inactivating a gene in a host cell. In some embodiments, the method of producing a host cell comprises determining the level of CpD gene inactivation, wherein a level of CpD expression is determined after using a CRISPR system to inactive the CpD gene in a host cell. In some embodiments, the method of producing a host cell comprises determining the level of CpD gene inactivation, wherein a level of CpD expression is determined after using a TALEN system to inactive the CpD gene in a host cell. In some embodiments, the method of producing a host cell comprises determining the level of CpD gene inactivation, wherein a level of CpD expression is determined after using a ZFN system to inactive the CpD gene in a host cell. In some embodiments, the method of producing a host cell comprises determining the level of CpD gene inactivation, wherein a level of CpD expression is determined after using a meganuclease system to inactive the CpD gene in a host cell.

In some embodiments, the CpD expression level is determined at the DNA level. In some embodiments, the CpD expression level is determined at the RNA level. In some embodiments, the method of producing a host cell comprises determining the CpD expression level using PCR. In some embodiments, the method of producing a host cell comprises determining the CpD expression level using PCR, wherein a variant sequence is detected. In some embodiments, the method of producing a host cell comprises determining the CpD expression level using qPCR. In some embodiments, the method of producing a host cell comprises determining the CpD expression level using qPCR.

In some embodiments, the CpD expression level is determined at the protein level. In some embodiments, the method of producing a host cell comprises determining the CpD expression level using immunohistochemistry. In some embodiments, the method of producing a host cell comprises determining the CpD expression level using Western blot. In some embodiments, the method of producing a host cell comprises determining the CpD expression level using flow cytometry.

In some embodiments, the level of CpD gene inactivation is determined by comparing the level of CpD expression after CpD gene inactivation to a control value. In some embodiments, the level of CpD gene inactivation is determined by comparing a level of CpD expression after CpD gene inactivation to a level of CpD expression prior to CpD gene inactivation.

Also provided are methods of evaluating a host cell for suitability of expression of Fc-containing proteins comprising determining CpD expression, wherein a reduced level of CpD expression is indicative of suitability.

Methods of Making a Fc-Containing Protein

The present application provides methods of making Fc-containing proteins described in the embodiments herein.

In some embodiments, the method of making a Fc-containing protein comprises: a) culturing the host cell; and b) obtaining the Fc-containing protein expressed by the host cell.

In some embodiments, the method of making a Fc-containing protein comprises: a) transforming a host cell with an expression vector comprising a nucleic acid encoding the Fc-containing protein; b) culturing the host cell; and c) obtaining the Fc-containing protein expressed by the host cell.

Methods for transforming a host cell using an expression vector are well known in the art. See, for example, Kim et al., *Anal Bioanal Chem,* 397, 2010. Method for transfecting a host cell including, but are not limited to, transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan.

Expression systems and constructs in the form of plasmids, expression vectors, transcription or expression cassettes which comprise at least one Fc-containing protein described herein are also provided. In certain embodiments, a plasmid, expression vector, transcription or expression cassette provided herein comprises a polynucleotide encoding at least one Fc-containing protein.

In some embodiments, expression vectors used in the host cells will contain sequences for plasmid maintenance and for cloning and expression of exogenous nucleotide sequences. Such sequences, collectively referred to as “flanking sequences,” in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the Fc-containing protein to be expressed, and a selectable marker element. Each of these sequences is discussed below.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part expression vectors purchased commercially, and the origin aids in the amplification of the vector in a host cell. If the vector of choice does not contain an origin of replication site, one may be chemically synthesized based on a known sequence, and ligated into the vector. For example, various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody light or heavy chain. As a result, increased quantities of a polypeptide are synthesized from the amplified DNA.

A ribosome-binding site is usually necessary for translation initiation of mRNA and is characterized by, for example, a Kozak sequence. The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

Expression and cloning vectors of the invention will typically contain a promoter that is recognized by the host organism and operably linked to the molecule encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding e.g., heavy chain or light chain, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thomsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42; or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Omitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315: 115-122); the immunoglobulin gene control region that is active in lymphoid cells (Grosschedl et al., 1984, *Cell* 38:647-658; Adames et al., 1985, *Nature* 318: 533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feta-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1: 161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234: 1372-1378).

An enhancer sequence may be inserted into the vector to increase transcription of DNA encoding light chain or heavy chain of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alphafeto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-I receptor signal peptide described in U.S. Pat. No. 4,968,607; the type II interleukin-I receptor signal peptide described in EP Patent No. 0 460 846.

The vector may contain one or more elements that facilitate expression when the vector is integrated into the host cell genome. Examples include an EASE element (Aldrich et al. 2003 *Biotechnol Prog.* 19: 1433-38) and a matrix attachment region (MAR). MARs mediate structural organization of the chromatin and may insulate the integrated vector from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors provided by the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding a Fc-containing protein sequence has been inserted into the proper site of the vector, the completed vector may be inserted into a suitable host cell for amplification and/or polypeptide expression.

Methods for making a vector comprising a nucleic acid encoding a Fc-containing protein are well known in the art. See, e.g., U.S. Pat. No. 7,923,221.

Construction of suitable vectors comprising a Fc-containing protein and the desired coding and control sequences employ standard ligation techniques. Isolated plasmids or DNA fragments are cleaved, tailored, and religated in the form desired to form the plasmids required. The methods employed are not dependent on the DNA source, or intended host.

In some embodiments, the method of making a Fc-containing protein further comprises determining an optimal ratio of the polynucleotide for introduction into a host cell. In some embodiments, mass spectrometry is used to determine Fc-containing protein yield, and the ratio is adjusted to maximize Fc-containing protein yield. In some embodiments, dual antigen ELISA is used to determine Fc-containing protein yield, and the ratio is adjusted to maximize Fc-containing protein yield.

Methods for culturing a host cell are well known to those in the art. See, e.g., Li et al., *MAbs,* 2, 2010. The host cells used to produce a desired Fc-containing protein of the embodiments herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth Enz,* 58, 1979, Barnes et al., *Anal Biochem,* 102, 1980, U.S. Pat. No. 4,767,704; 4,657,866; 4,927,762; 4,560,655; or 5,122,469; International Patent Application Nos. WO 90/03430 or WO 87/00195; or U.S. Pat. Reissue No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Generally, the production of Fc-containing proteins is done on a large scale (such as a commercial scale). To achieve a population of a host cell suitable for commercial scale production, one of ordinary skill in the art will recognize the utility using a stepwise approach to expanding a host cell population. For example, the process involves growing a desired host cell on a smaller scale to allow for an increase in the host cell population, such as a seed train. To further increase the population of the host cell, methods generally involved using the seed train to inoculate a larger culture tank, such as an inoculum tank. Often, a series of inoculum tanks of increasing size are used to expand the population of a host cell, such as an inoculum train. This process will provide a suitable population of a host cell for culture in a production culture. In some embodiments, the production culture is a 1000 L culture tank.

In some embodiments, the method of making a Fc-containing protein comprises culturing the host cell using a batch feed method. In some embodiments, the method of making a Fc-containing protein comprises culturing the host cell using a continuous feed method. In some embodiments, the method of making a Fc-containing protein comprises culturing the host cell using a feed method comprising a batch feed method and a continuous feed method.

Methods for obtaining a Fc-containing protein are well known in the art. See, e.g., Huse et al., *J Biochem Bioph Meth,* 51, 2002. Fc-containing proteins can be produced intracellularly or directly secreted into the medium. If the Fc-containing proteins are produced intracellularly, as a first step, the particulate debris, either host cells or lysed fragments, are removed, for example, by centrifugation or ultrafiltration. If the Fc-containing proteins are secreted into the medium, supernatants from such expression systems are generally first concentrated using a commercially available protein concentration filter, for example, an Amicon or Millipore Pellicon ultrafiltration unit. In some embodiments, a protease inhibitor may be included in any of the foregoing steps to inhibit proteolysis and antibiotics may be included to prevent the growth of adventitious contaminants.

The composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the Fc-containing protein. Protein A can be used to purify Fc-containing proteins that are based on human immunoglobulins containing 1, 2, or 4 heavy chains (See, e.g., Lindmark et al., *J Immunol Meth,* 62, 1983). Protein G is recommended for all mouse isotypes and for human 3 (See, e.g., Guss et al., *EMBO,* 5, 1986). The matrix to which the affinity ligand is attached is often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the Fc-containing protein to be recovered.

In some embodiments, the method of purifying a Fc-containing protein comprises using a filter. In some embodiments, the filter is a diafiltration system. In some embodiments, the filter is an ultrafiltration system. In some embodiments, the filter is a viral filtration system. In some embodiments, the purifying a Fc-containing protein comprises using a series of filtration steps. In some embodiments, the series of filtration steps is selected from at least one of the following: diafiltration, ultrafiltration, and viral filtration.

In some embodiments, the method of purifying the Fc-containing protein comprises using a series of protein purification techniques selected from filtration, protein A purification, cation exchange purification, strong cation exchange purification, anion exchange purification, reverse phase purification, and multimodal purification.

Also provided in the present application are methods of determining C-terminal lysine presence. In some embodiments, the method of determining C-terminal lysine presence comprises using isoelectric focusing, such as imaged capillary isoelectric focusing. In some embodiments, the method of determining C-terminal lysine presence comprises using mass spectrometry.

Methods of Treatment

The present application provides methods of treating a disease in an individual in need thereof comprising administering to the individual a pharmaceutical composition described in the embodiments herein.

In some embodiments, an effective amount of a plurality of Fc-containing proteins is administered to the individual in need thereof, wherein substantially all of the plurality of Fc-containing proteins has a C-terminal lysine on each Fc domain.

The pharmaceutical composition described herein can be administered via various routes, such as parenterally, including intravenous, intra-arterial, intraperitoneal, intrapulmonary, oral, inhalation, intravesicular, intramuscular, intratracheal, subcutaneous, intraocular, intrathecal, or transdermal. In some embodiments, pharmaceutical composition described herein can be administered parenterally. In some embodiments, pharmaceutical composition described herein can be administered intravenously. In some embodiments, pharmaceutical composition described herein can be administered subcutaneously. In some embodiments, pharmaceutical composition described herein can be administered locally. In some embodiments, pharmaceutical composition described herein can be administered topically.

The diseases that can be treated by the methods herein are any disease that can be treated with a Fc-containing protein. In some embodiments, the disease a cancer. In some embodiments, the disease is an autoimmune disease. In some embodiments, the disease is an infection.

In some embodiments, the pharmaceutical composition described herein is used in combination with another administration modality or treatment.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Carboxypeptidase D is Responsible for C-Terminal Lysine Cleavage in Chinese Hamster Ovary (CHO) Cells Methods:

Cell line A is an in-house developed antibody-producing (IgG) cell line derived from DUXB-11-based DHFR deficient DP12 host. See, Hu et al., *Biotechnol Prog,* 29, 2013; Urlaub et al., *Proc Natl Acad Sci,* 77, 1980. Cell line B is an in-house developed antibody-producing (IgG) cell line derived from CHOK1 host. See, Hu et al., *Biotechnol Prog,* 29, 2013. CHO cells were cultured in a proprietary DMEM/F12-based medium in 125 ml shake flask vessels at 150 rpm, 37° C. and 5% $CO_2$. Cells were passaged with a seeding density of $3\times10^5$/mL every three to four days.

Total RNA was isolated using a RNeasy 96 kit (Cat# 74181, Qiagen, Valencia, Calif.) and treated with DNase digestion (Cat# 79254, RNase free DNase kit, Qiagen, Valencia, Calif.) to remove any residual DNA that may be present in the isolated RNA sample. Taqman was performed using a universal qRT-PCR master mixture according to the manufacturer's instruction (Cat# 4309169, Applied Biosystems, Foster City, Calif.). Expression levels of different carboxypeptidases were normalized to the housekeeping gene, β-2-microglobulin (β2m).

Primer and probe sequences used for Taqman analysis were as follows:

```
CpD forward primer:
                                        (SEQ ID NO. 1)
CCC ACA CAT TAC AAA TCT TAC CA;

CpD reserve primer:
                                        (SEQ ID NO. 2)
GAG ATT TCG AGG GAC CAA AT;

CpD probe:
                                        (SEQ ID NO. 3)
TTG GGA CAG AGT GCT GAG TAT CGT CA;

CpN forward primer:
                                        (SEQ ID NO. 4)
GTG GGA TCA ATC ACG ATG TC;

CpN reserve primer:
                                        (SEQ ID NO. 5)
CCT TGG CAG TGA CAA TGT AAG TA;

CpN probe:
                                        (SEQ ID NO. 6)
ACA TGG GGA TTA CTT CCG TCT GCT G;

CpM forward primer:
                                        (SEQ ID NO. 7)
AAC TTG GAG AGT ACT ACC TGC TTC T;

CpM reserve primer:
                                        (SEQ ID NO. 8)
TCA TGC CCA GGG ACT GTA;

CpM probe:
                                        (SEQ ID NO. 9)
ATT GAT CAC GTA GGA CCC TGG CAA A;

CpB forward primer:
                                       (SEQ ID NO. 10)
TGA ATG CGC TGG TGA AAG G;

CpB reserve primer:
                                       (SEQ ID NO. 11)
TCC TGG GCC ATA TGT GTA CTT G;

CpB probe:
                                       (SEQ ID NO. 12)
CGG TCA AGG AAC TTG CCT CTC TGC A;

CpE forward primer:
                                       (SEQ ID NO. 13)
TGG CTA CCT GGC AAT AAC AA;

CpE reserve primer:
                                       (SEQ ID NO. 14)
CGA CTC CAG CTC AAA GTC AA;

CpE probe:
                                       (SEQ ID NO. 15)
AAG TGG CAG TTC CTT TCA AGC CTG C;

β-microglobulin forward primer:
                                       (SEQ ID NO. 16)
TCC TCT CAG TGG TCT GCT TGG;

β-microglobulin reserve primer:
                                       (SEQ ID NO. 17)
TGG CGT GTG TAG ACT TGC ACT T;

β-microglobulin probe:
                                       (SEQ ID NO. 18)
TGC CAT CCA GCG TCC CCC A.
```

All primers and probes were synthesized and purified at Genentech (Redwood City, Calif.).

Western blot analysis was performed to determine the relative carboxypeptidase D protein expression levels in CHO cells. β-actin, a cytosolic protein, was used as the sample loading control. Cell pellets were collected and lysed in 1× cell lysis buffer (Cat# 9803, Cell Signaling Technology, Danvers, Mass.). Total protein of the lysed supernatants was quantified by Bradford assay (Cat# 1856210, Thermo Scientific, Rockford, Ill.), and heated at 95° C. for 3 minutes before loading onto a reducing SDS-PAGE gel. Separated proteins were transferred to a nitrocellulose membrane by electroblotting. Transferred membranes were then incubated with a rabbit polyclonal antibody against carboxypeptidase D (Cat# SAB2700486, Sigma, Saint Louis, Mo.) to detect CpD protein expression and a mouse antibody (Cat# A2228, Sigma, Saint Louis, Mo.) against β-actin as a loading control for equal sample loading.

Designer of Small Interfering RNA (DSIR) program (http://www.biomedcentral.com) was used to design CpD and CpN-specific small interfering RNA (siRNA) sequences:

```
CpD siRNA target sequence:
                                    (SEQ ID NO. 19)
GGAAGAGAACTGCTACTAA;

CpN siRNA target sequence:
                                    (SEQ ID NO. 20)
GAATGGTGCTTGATGAGAA.
```

The above siRNA sequences were synthesized and individually cloned into the pSilencer 3.1-H1vector (Cat# AM5766, Ambion, Austin, Tex.) to make siRNA expression constructs. Each construct was introduced to antibody-expressing cell line A and antibody-expressing cell line B using lipofectamine 2000 CD according to the manufacturer's recommendation (Invitrogen, Carlsbad, Calif.) in transient transfection. 24 hours post transfection, cell pellets were collected to assess each carboxypeptidase mRNA expression by Taqman. Additionally, Cell Culture Fluid (CCF) was collected and concentrated by Amicon Ultra-15 (30,000 MWCO, Millipore, Bedford, Mass.) for charge variant product quality analysis by Imaged Capillary Isoelectric Focusing (IcIEF).

Charge variant distribution was assessed by using an iCE280 analyzer (ProteinSimple) with a fluorocarbon coated capillary cartridge (100 μm×5 cm). The ampholyte solution consisted of a mixture of 0.35% methyl cellulose (MC), 1.34% 3-10 carrier ampholytes, 1.34% 6.7-7.7 carrier ampholytes, pI markers (pI 6.61 and pI 9.22), and 10 mM L-arginine free base in purified water. The anolyte was 80 mM phosphoric acid, and the catholyte was 100 mM sodium hydroxide, both in 0.1% MC. Samples were diluted, mixed with the ampholyte solution, and then focused by introducing a potential of 1500 V for 1 minute, followed by a potential of 3000 V for 8 minutes. An image of the focused charge variants was obtained by passing 280 nm ultraviolet light through the capillary and into the lens of a charge coupled device digital camera. In order to remove heavy chain C-terminal Lys residue, carboxypeptidase B was added to each sample at the dilution step at an enzyme-to-substrate ratio of 1:100 (w/w) followed by incubation at 37° C. for 20 minutes.

The following guide RNA (gRNA) sequences below were designed to sit on CpD exon 2 and exon 21, respectively:

```
CpD guide RNA1 sequence (gRNA 1) for exon 2:
                                    (SEQ ID NO. 21)
GAA GAC GAG ACT TTC AAA GAC GG;
```

-continued

```
CpD guide RNA2 sequence (gRNA 2) for exon 21:
                                    (SEQ ID NO. 22)
TCA GTT AGG TGG CTT AGG TTC GG.
```

When co-transfected along with caspase 9 (Cas9), the gRNA sequences are expected to enable a ~46 kb deletion encompassing a majority of the annotated CpD locus.

Individual gRNAs were cloned and transcribed under the control of the human U6 promoter of the pLKO.5 vector (Cat# SHC-201, Sigma, St. Louis, Mo.). The two gRNAs and Cas9 constructs were co-transfected at an equimolar ratio. 72 hours post transfection, cells were seeded into 384-well plates by limiting dilution. Three weeks later, colonies were picked and transferred to 96-well plates and screened by Polymerase Chain Reaction (PCR). PCR primers for screening CpD knockout (~46 kb deletion) and wild type alleles were as follows:

```
Forward primer for CpD knockout allele:
                                    (SEQ ID NO. 23)
AGT TCA TTT ATG AAA GAT CCT GTG G;

Reverse primer for CpD knockout allele:
                                    (SEQ ID NO. 24)
GGA AAG GAG TCC TTC AGT GAA CAC;

Forward primer for CpD wild type allele:
                                    (SEQ ID NO. 25)
CCA GTT CTG CTG TTA CAC TTT GAG;

Reverse primer for CpD wild type allele:
                                    (SEQ ID NO. 26)
AAT GTT TCC TCT TTC CTG GAC CTT;
```

Diluted protein samples (1 mg/mL) were mixed with a 20 mg/mL TCEP solution at 1:1 ratio and incubated for 10 minutes at 60° C. to reduce and dissociate antibodies into light and heavy chains. Each sample was then analyzed by liquid chromatography electrospray ionization mass spectrometry (LC-ESI-MS) using an Agilent 6210 time-of-flight mass spectrometer coupled with a nano-Chip LC-ESI source. Briefly, about 5 ng of protein samples was injected onto a custom chip with a 40 nL trap column for desalting and an equivalent analytical column dimensions of 43 mm×75 m, Zorbax 300SB-C8 (5 m, Agilent Technologies, Santa Clara, Calif.) for separation at 400 nL/min. See, Lu et al., *Mabs,* 5, 2013. Mobile phase A was 0.1% formic acid in water and mobile phase B was 0.1% formic acid in acetonitrile. MS data was extracted and deconvoluted using Agilent MassHunter Quantitative Analysis Workstation Software B.04.00. To estimate the percentage of C-terminal lysine, the intensity of deconvoluted mass corresponding to antibody heavy chains with or without C-terminal lysine was used.

Fed-batch production was performed in shake flask vessels in proprietary chemically defined medium with bolus feeds on days 3, 7, and 10. A temperature shift from 37° C. to 35° C. was carried out on day 3. Day 14 titers were determined using protein A affinity chromatography with UV detection.

Results:

qPCR analysis was performed to measure mRNA levels of possible endogenous carboxypeptidases in DUXB-11 based DHFR deficient DP12, DHFR positive CHOK1 hosts, and antibody-producing cell lines from each host (cell line A and cell line B). Cell line A was derived from DHFR deficient DP12 host and cell line B was derived from DHFR positive CHOK1 host.

Figure 1B:
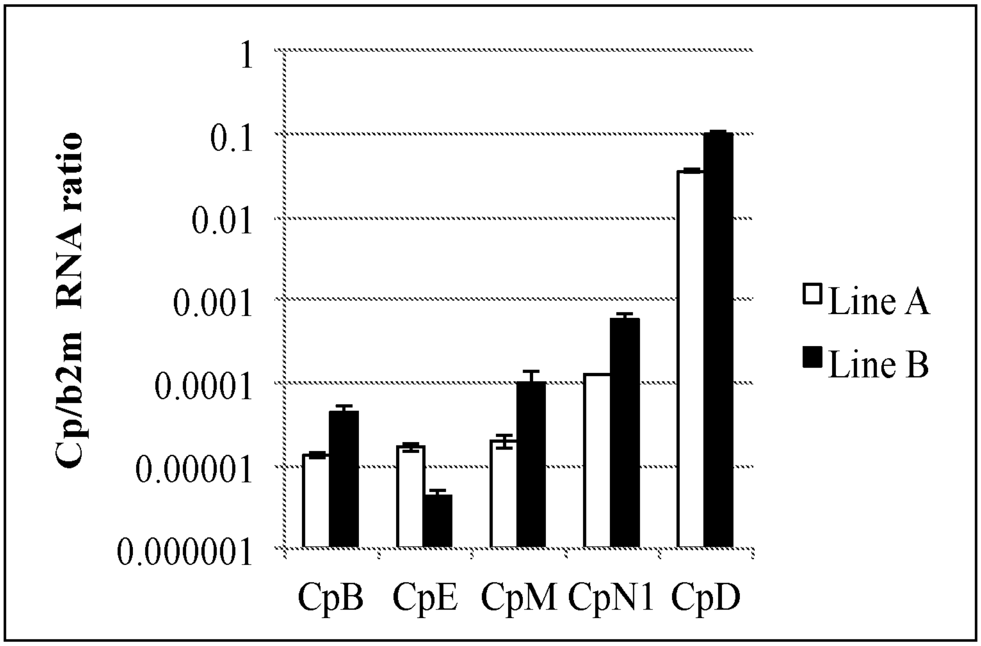
Figure 2A:
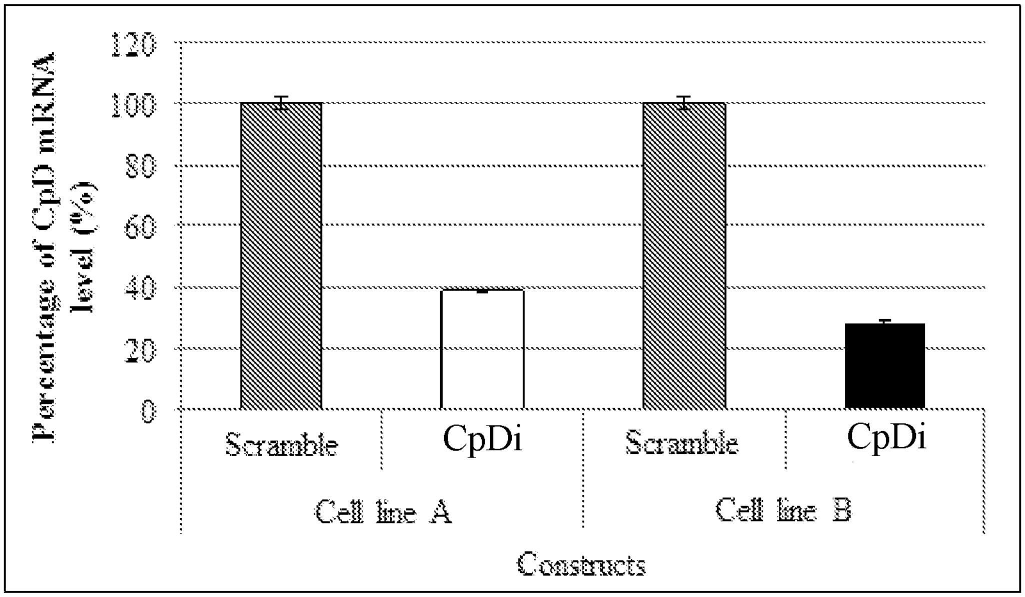
FIGS. 2A-2B shows the level of carboxypeptidase mRNA expression following transfection with a carboxypeptidase specific siRNA construct in antibody-expressing cell line A (white bars) and antibody-expressing cell line B (black bars). Each error bar denotes 1 standard deviation.
Figure 2B:
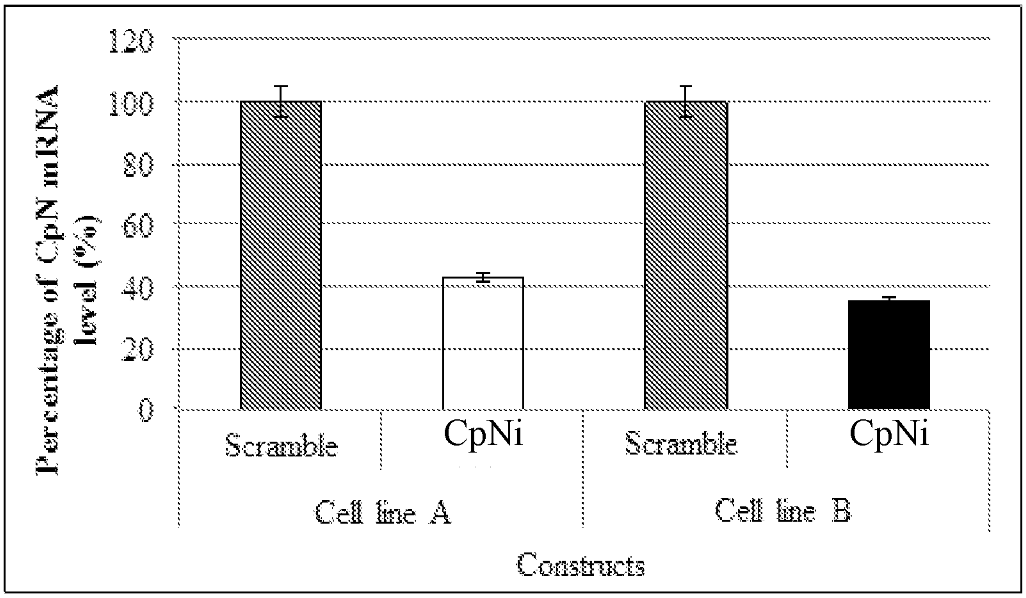

5 carboxypeptidases, CpD, CpN, CpM, CpB, and CpE, were chosen for mRNA expression analysis by qPCR. CpD had the highest mRNA expression levels in both CHO hosts and their respective antibody-expressing lines (FIG. 1A and FIG. 1B). CpD and CpN mRNA levels were higher than those for CpM, CpE, and CpB in cell line A and cell line B (FIG. 1B).

siRNA-mediated knockdown (See, e.g., Rao et al., *Adv Drug Deliv Rev,* 61, 2009) experiments were performed using the two antibody-producing cell lines with the two most abundant carboxypeptidases, namely, CpD and CpN. Each cell line was transiently transfected with a siRNA construct specifically targeting CpD (CpDi construct) or CpN (CpNi construct), respectively. A scrambled vector control construct was also transfected as a negative control. As shown in FIG. 2A, CpD mRNA levels were knocked down to 39% in cell line A and 28% in cell line B. Similar results were observed with regard to CpN mRNA inhibition by CpNi construct, where CpN mRNA level was reduced to 43% in cell line A and 35% in cell line B (FIG. 2B).

Figure 3:
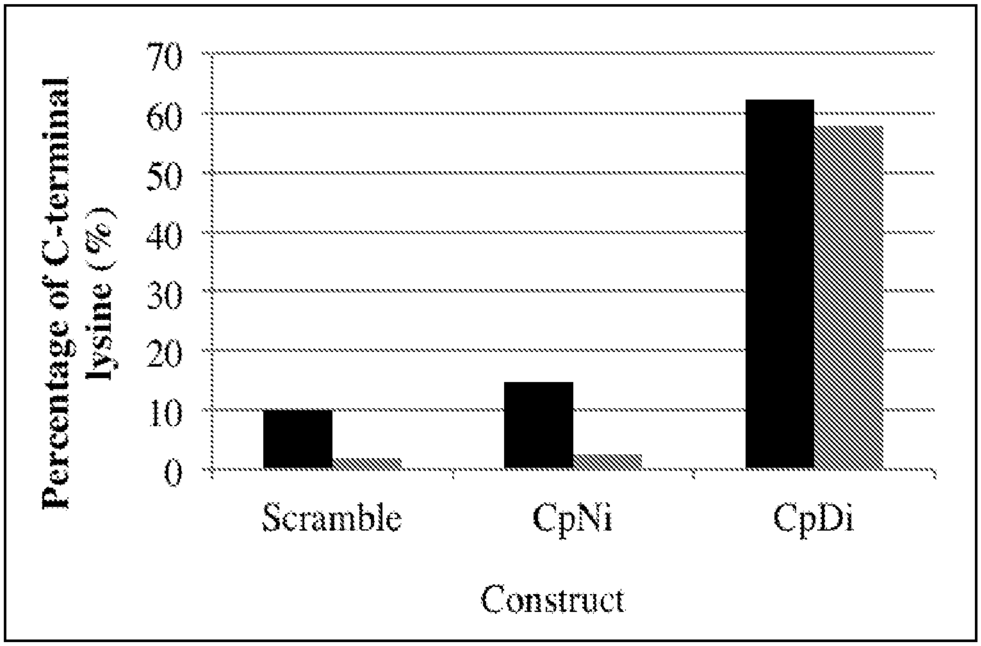
FIG. 3 shows C-terminal lysine levels of an expressed antibody following transfection with a carboxypeptidase specific siRNA construct in antibody-expressing cell line A (black bars) and antibody-expressing cell line B (grey bars).

The percentage of C-terminal lysine present on the antibody in cell culture was calculated. To calculate the percentage of C-terminal lysine present on the antibody in cell culture, supernatants from CpDi and CpNi transfected cell lines, with and without CpB treatment, were purified by protein-A affinity chromatography and analyzed by Imaged Capillary Isoelectric Focusing (IcIEF). The differential value between CpB treated and untreated samples represents the percentage of antibody that has intact C-terminal lysines. Significantly increased C-terminal lysine levels were observed in both cell lines when CpD mRNA was knocked down to approximately 30-40% (FIG. 2A and FIG. 3). Minimal C-terminal lysine level changes were observed in the two cell lines transfected with either the scrambled RNAi construct (negative control) or the CpNi construct which knocked down CpN mRNA to approximately 40% (FIG. 2B and FIG. 3). These results demonstrated that reduction in CpD mRNA levels led to increased C-terminal lysine levels, while changes in CpN mRNA levels had no effect on C-terminal lysine in the two tested antibody-producing lines.

Figure 4A:
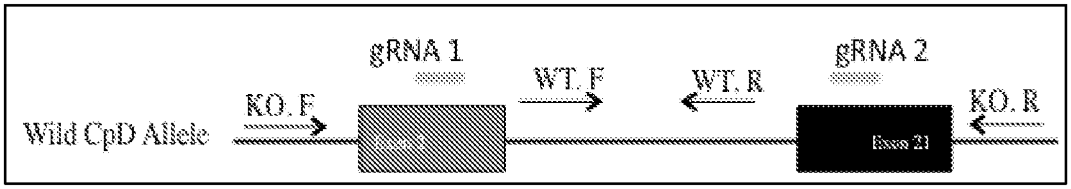
FIGS. 4A-4B shows schematic diagrams of wild type (WT) and knockout (KO) CpD alleles.
Figure 4B:
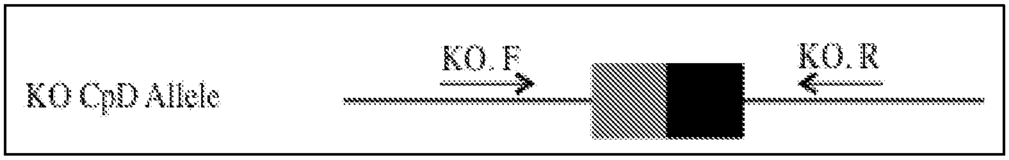
Figure 5A:
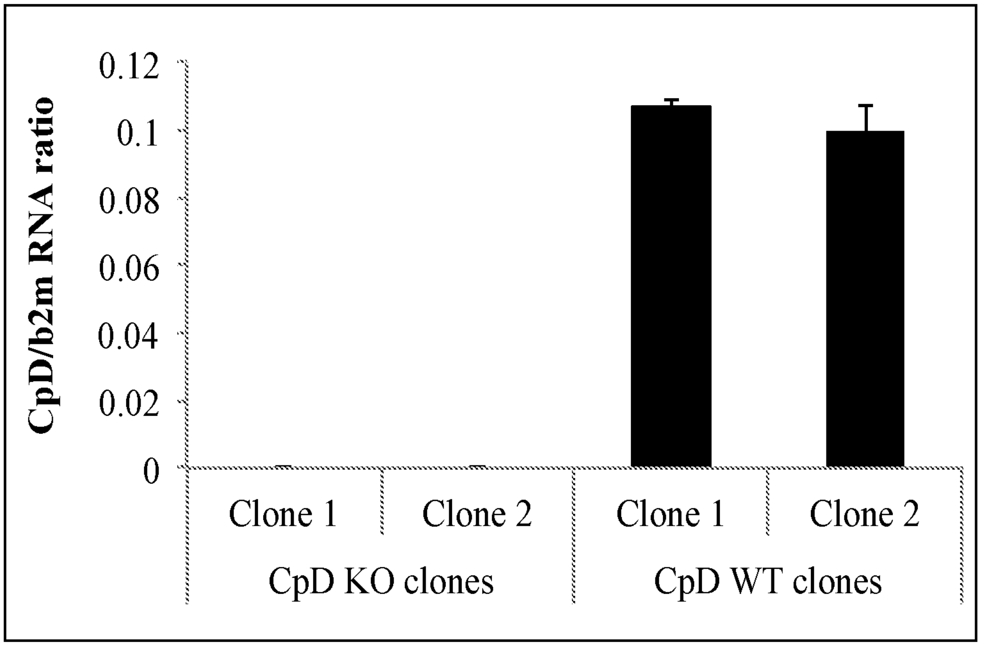
FIGS. 5A-5B shows CpD expression levels in two CpD knockout clones from the antibody-expressing cell line B.
Figure 5B:
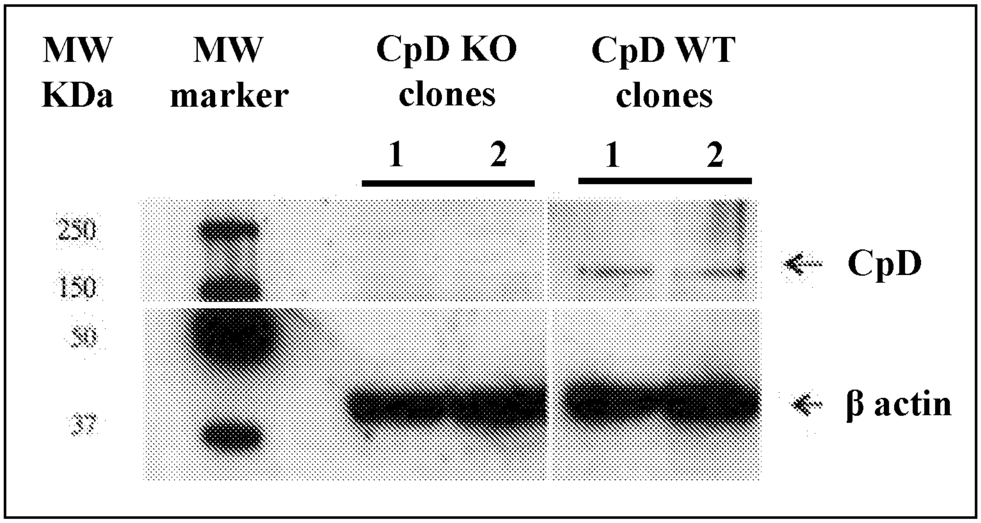

A knockout experiment using CRISPR technology (see, e.g., He et al., *Biotechnol Bioeng,* 2014; Jinek et al., *Elife,* 2, 2013) was performed. The known CHOK1 CpD genomic sequence in NCBI database is approximately 55 kb including most of the coding region sequences for CHO CpD. Two guide RNA sequences were designed to simultaneously target exon 2 and 21 of the Chinese hamster CpD gene aiming to delete the 46 kb sequence between the two exons as illustrated in FIG. 4A. When the two gRNA constructs and Cas9 endonuclease construct were co-transfected into the antibody-expressing cell line B, Cas9 endonuclease cleaves specific DNA sequences that are complimentary to the gRNAs. This cleavage leads to double-strand DNA breaks and subsequent non-homologous end-joining (NHEJ) DNA repair with deletions or insertions that can abolish expression of a target gene. Using PCR primers adjacent and upstream of the gRNA sequences, CpD knockout cells should yield a PCR product of approximately 600 base pairs when the intervening sequences between the two gRNAs are deleted as illustrated in FIG. 4B. A total of 180 clones were screened for the CpD sequence deletion, and based on PCR product sizes and sequence analysis, two clones with both CpD alleles deleted were obtained and used for CpD mRNA and protein expression analysis (data not shown). As shown in FIG. 5A, CpD mRNA was undetectable in the two CpD KO clones by qPCR analysis. Furthermore, Western blot analysis using the anti-CpD antibody showed that a protein with the molecular weight of approximately 180 kDa was absent in two CpD KO clones, but present in CpD WT clones as shown in FIG. 5B.

Figure 6A:
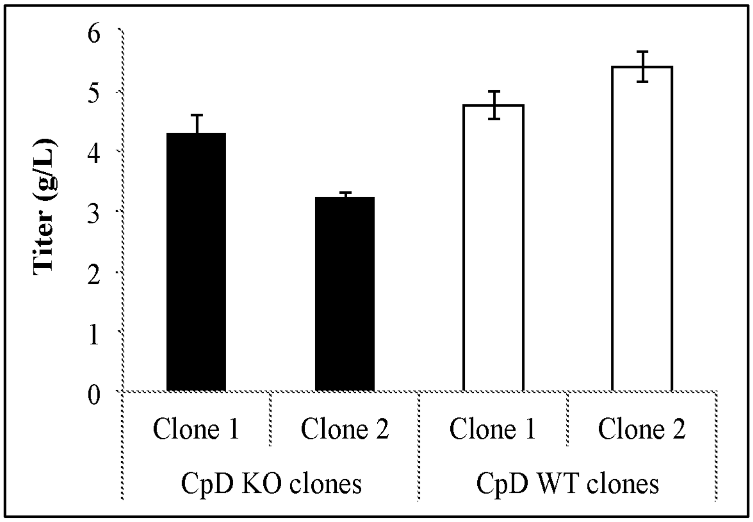
FIGS. 6A-6C shows fed-batch shake flask evaluation data of two CpD KO clones and two CpD WT clones of antibody-producing cell line B. Each bar represents the average from two replicates. Each error bar denotes 1 standard deviation.
Figure 6B:
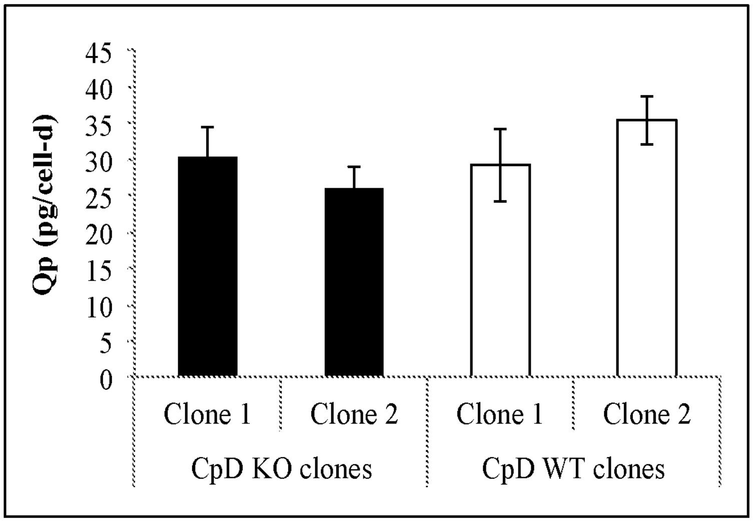
Figure 6C:
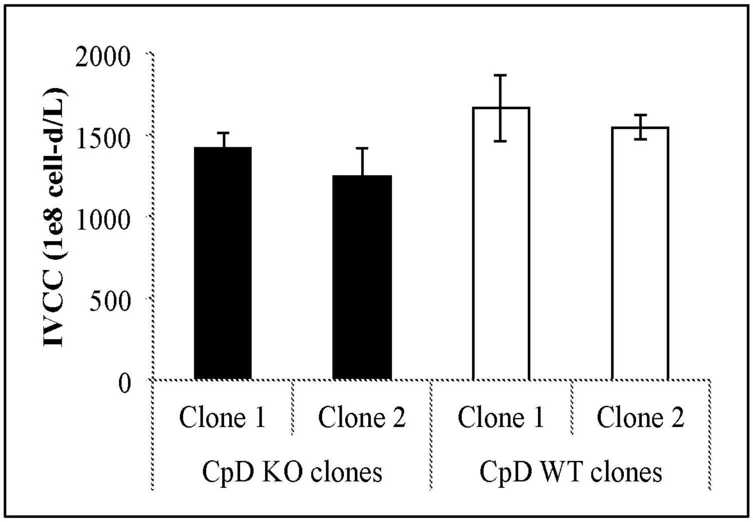
Figure 7:
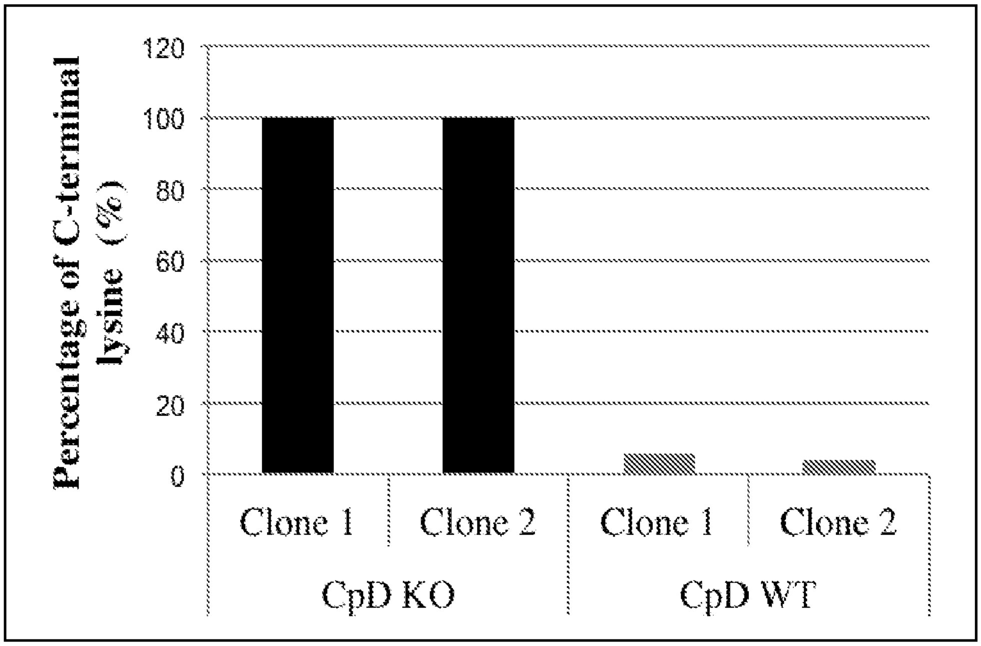
FIG. 7 shows C-terminal lysine levels in two CpD KO clones and two CpD WT clones of antibody-producing cell line B.

CpD KO and WT clones were evaluated for productivity and product quality attributes. No obvious differences were observed in integrated viable cell count cell (IVCC), specific productivities (Qp), and titers among two KO and two WT clones (FIG. 6), indicating that absence of CpD expression in CHO cells did not impact cell productivity and growth as assessed by the fed-batch shake flask production assay. Importantly, C-terminal lysine level was measured by mass spectrometry-based analysis of reduced antibody showing that approximately 4-6% C-terminal lysine was observed in the two WT clones, whereas 100% of C-terminal lysine was present in the two KO clones (FIG. 7). Thus, it was demonstrated that CpD is the only carboxypeptidase which is responsible for removing C-terminal lysine of an antibody heavy chain in CHO cells. The same result was also observed by an IcIEF assay (data not shown). Other product quality attributes and cell culture metabolite profiles were comparable between CpD KO and WT clones (data not shown).

What is claimed is:

1. A Chinese hamster ovary (CHO) host cell for production of a Fc-containing protein comprising a C-terminal lysine, wherein the CHO host cell has the carboxypeptidase D (CpD) gene knocked out, wherein the CpD gene is knocked out using a CRISPR system, a transcription activator-like effector nuclease (TALEN) system, a zinc-finger nuclease (ZFN) system, or a meganuclease system, and wherein the host cell comprises an expression vector comprising a nucleic acid encoding the Fc-containing protein comprising the C-terminal lysine.

2. The host cell of claim 1, wherein the Fc-containing protein is an antibody or a Fc-containing fusion protein.

3. The host cell of claim 1, wherein the CpD gene is knocked out by gene deletion, addition, or substitution.

4. A cell culture system comprising the host cell of claim 1.

5. The host cell of claim 1, wherein the Fc-containing protein has a C-terminal sequence of proline-glycine-lysine.

6. A method of producing a Chinese hamster ovary (CHO) host cell for production of a Fc-containing protein comprising a C-terminal lysine, wherein the CHO host cell has the carboxypeptidase D (CpD) gene knocked out, the method comprising:

knocking out the CpD gene in a CHO host cell having the carboxypeptidase D (CpD) gene, wherein the CpD gene is knocked out using a CRISPR system, a transcription activator-like effector nuclease (TALEN) system, a zinc-finger nuclease (ZFN) system, or a meganuclease system; and introducing an expression vector comprising a nucleic acid encoding an Fc-containing protein comprising a C-terminal lysine, thereby producing the CHO host cell for production of the Fc-containing protein comprising a C-terminal lysine.

7. The method of claim 6, wherein the CpD gene is inactivated knocked out by gene deletion, addition, or substitution.

8. A method of making a Fc-containing protein comprising:

a) culturing the host cell of claim 1;

b) obtaining the Fc-containing protein expressed by the host cell.

* * * * *